(12) United States Patent
Brumfield et al.

(10) Patent No.: US 7,744,598 B2
(45) Date of Patent: *Jun. 29, 2010

(54) REDUCING INSTRUMENT FOR SPINAL SURGERY

(75) Inventors: David L. Brumfield, Collierville, TN (US); Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1157 days.

This patent is subject to a terminal disclaimer.

(21) Appl. No.: 11/236,339

(22) Filed: Sep. 27, 2005

(65) Prior Publication Data

US 2006/0166535 A1 Jul. 27, 2006

Related U.S. Application Data

(63) Continuation-in-part of application No. 11/043,318, filed on Jan. 26, 2005.

(51) Int. Cl.
*A61F 5/00* (2006.01)
(52) U.S. Cl. .................................. 606/86 A
(58) Field of Classification Search .............. 606/86 A, 606/96, 99, 103, 104, 205, 246, 282
See application file for complete search history.

(56) References Cited

U.S. PATENT DOCUMENTS

| | | | |
|---|---|---|---|
| 3,604,487 A | 9/1971 | Gilbert | |
| 3,844,291 A | 10/1974 | Moen | |
| 4,411,259 A | 10/1983 | Drummond | |
| 5,020,519 A | 6/1991 | Hayes et al. | |
| 5,113,685 A | 5/1992 | Asher et al. | |
| 5,217,497 A | 6/1993 | Mehdian | |
| 5,281,223 A * | 1/1994 | Ray | 606/86 A |
| 5,314,431 A | 5/1994 | Graziano | |
| 5,330,472 A | 7/1994 | Metz-Stavenhagen | |
| 5,364,397 A | 11/1994 | Hayes et al. | |
| 5,389,099 A | 2/1995 | Hartmeister et al. | |
| 5,449,361 A | 9/1995 | Preissman | |
| 5,458,608 A | 10/1995 | Wortrich | |
| 5,466,243 A | 11/1995 | Schmieding et al. | |
| 5,474,555 A | 12/1995 | Puno | |
| 5,554,157 A | 9/1996 | Errico | |
| 5,616,143 A | 4/1997 | Schlapfer et al. | |
| 5,647,873 A | 7/1997 | Errico | |

(Continued)

FOREIGN PATENT DOCUMENTS

DE 4238339 A1 5/1994

(Continued)

*Primary Examiner*—Thomas C Barrett
*Assistant Examiner*—Nicholas Woodall

(57) ABSTRACT

An instrument is provided for use in orthopedic surgery for reduction of a connecting member such as a spinal rod toward an implant such as a bone screw. An embodiment of the instrument includes handle portions that are pivotable relative to each other and biased apart, and arm portions pivotable relative to each other and to the handle portions. Distal portions of the arm portions, which may be offset from the arm portions, provide structure for engaging a connecting member and an implant. Squeezing the handle portions force the distal portions of the arm portions together, forcing together the connecting member and the implant. A toothed bar and pawl may be provided to retain the instrument in a squeezed state.

31 Claims, 15 Drawing Sheets

U.S. PATENT DOCUMENTS

| | | | |
|---|---|---|---|
| 5,690,630 A | 11/1997 | Errico | |
| 5,720,751 A | 2/1998 | Jackson | |
| 5,782,830 A | 7/1998 | Farris | |
| 5,810,878 A | 9/1998 | Burel et al. | |
| 5,817,094 A | 10/1998 | Errico | |
| 5,863,293 A | 1/1999 | Richelsoph | |
| 5,899,901 A | 5/1999 | Middleton | |
| 5,910,141 A | 6/1999 | Morrison et al. | |
| 5,944,720 A | 8/1999 | Lipton | |
| 5,964,760 A | 10/1999 | Richelsoph | |
| 6,010,503 A | 1/2000 | Richelsoph | |
| 6,036,692 A | 3/2000 | Burel et al. | |
| 6,042,582 A | 3/2000 | Ray | |
| 6,063,088 A | 5/2000 | Winslow | |
| 6,355,040 B1 | 3/2002 | Richelsoph | |
| 6,440,133 B1 | 8/2002 | Beale et al. | |
| 6,440,137 B1 | 8/2002 | Horvath et al. | |
| 6,443,953 B1 | 9/2002 | Perra et al. | |
| 6,471,705 B1 | 10/2002 | Biedermann et al. | |
| 6,520,963 B1 | 2/2003 | McKinley | |
| 6,530,929 B1 * | 3/2003 | Justis et al. | 606/103 |
| 6,551,316 B1 | 4/2003 | Rinner et al. | |
| 6,565,565 B1 | 5/2003 | Yuan et al. | |
| 6,599,294 B2 * | 7/2003 | Fuss et al. | 606/99 |
| 6,648,888 B1 | 11/2003 | Shluzas | |
| 6,660,006 B2 | 12/2003 | Markworth et al. | |
| 6,695,843 B2 | 2/2004 | Biedermann et al. | |
| 6,726,692 B2 | 4/2004 | Bette | |
| 6,746,449 B2 | 6/2004 | Jones et al. | |
| 6,755,829 B1 | 6/2004 | Bono et al. | |
| 6,843,791 B2 | 1/2005 | Serhan | |
| 7,090,679 B2 * | 8/2006 | Saint-Martin et al. | 606/99 |
| 7,320,689 B2 * | 1/2008 | Keller | 606/99 |
| 7,371,239 B2 * | 5/2008 | Dec et al. | 606/103 |
| 2002/0072752 A1 | 6/2002 | Zucherman et al. | |
| 2002/0095153 A1 | 7/2002 | Jones et al. | |
| 2003/0225408 A1 | 12/2003 | Nichols et al. | |
| 2004/0049191 A1 | 3/2004 | Markworth et al. | |
| 2004/0138662 A1 | 7/2004 | Landry et al. | |
| 2004/0147936 A1 | 7/2004 | Rosenberg et al. | |
| 2004/0172022 A1 | 9/2004 | Landry et al. | |
| 2004/0193160 A1 | 9/2004 | Richelsoph | |
| 2004/0249378 A1 | 12/2004 | Saint Martin et al. | |
| 2005/0154389 A1 | 7/2005 | Selover et al. | |
| 2005/0192587 A1 | 9/2005 | Lim | |
| 2006/0025768 A1 | 2/2006 | Lott et al. | |
| 2006/0166535 A1 | 7/2006 | Brumfield et al. | |

FOREIGN PATENT DOCUMENTS

WO     WO 93/11715     6/1993

\* cited by examiner

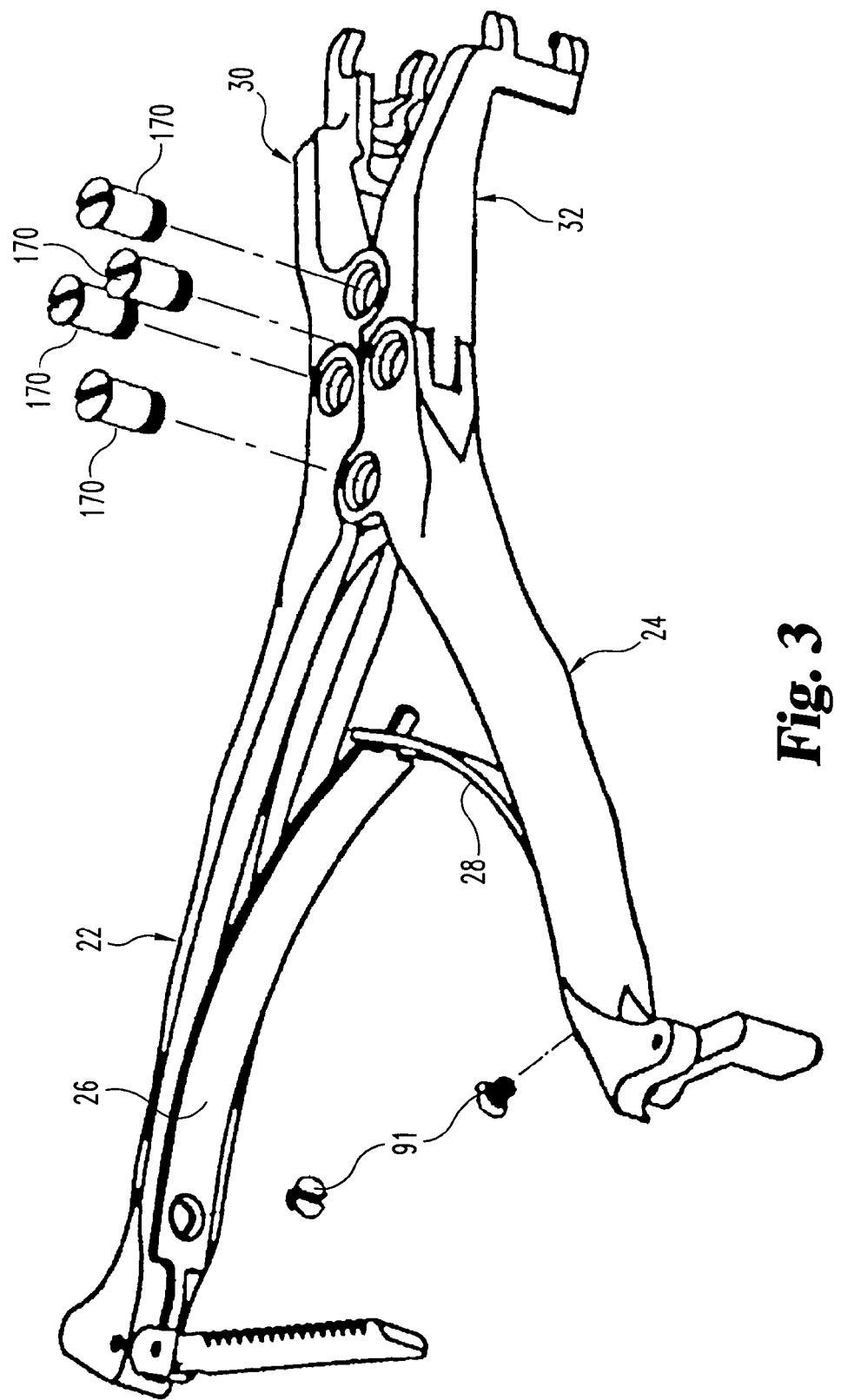

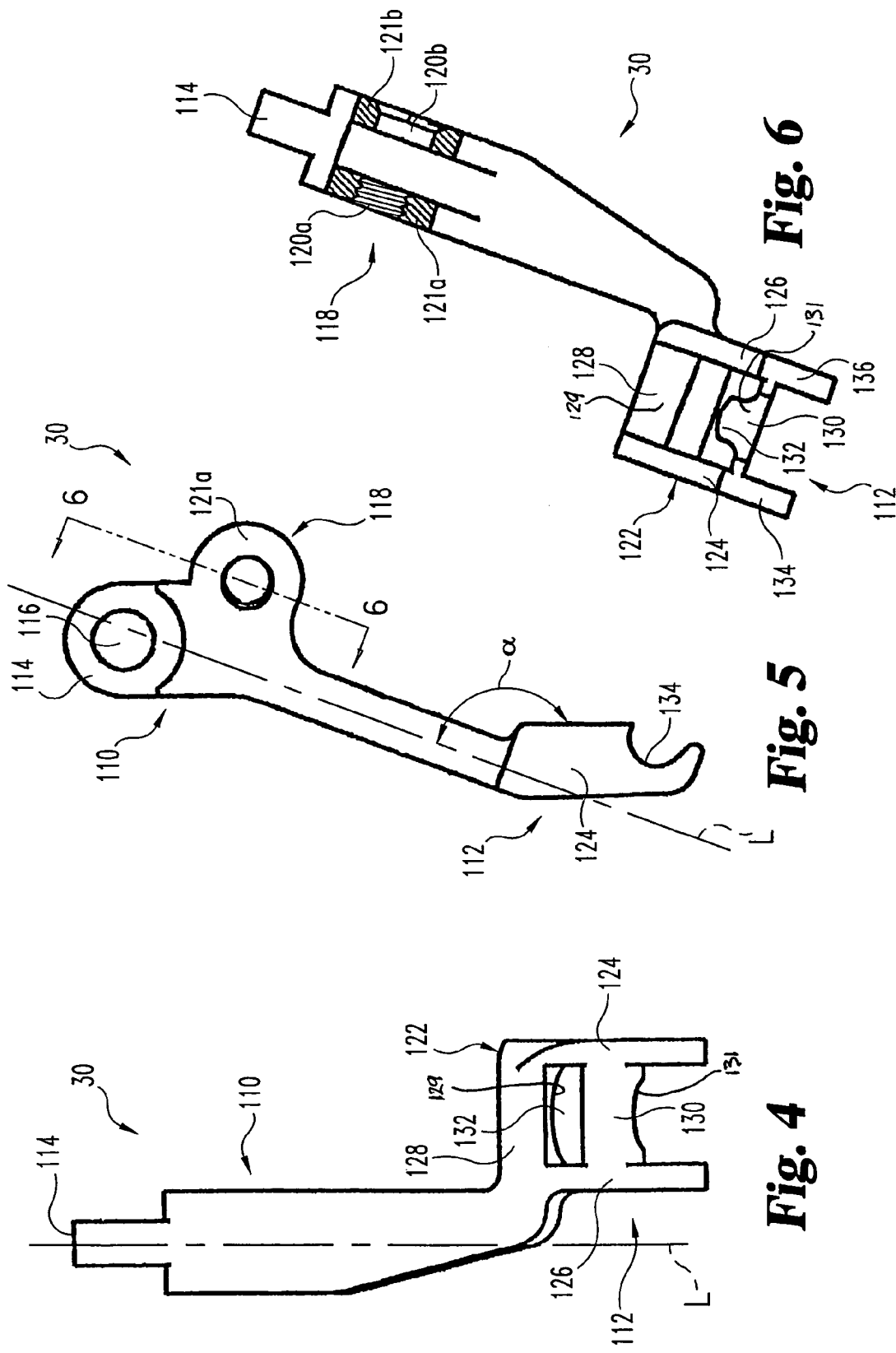

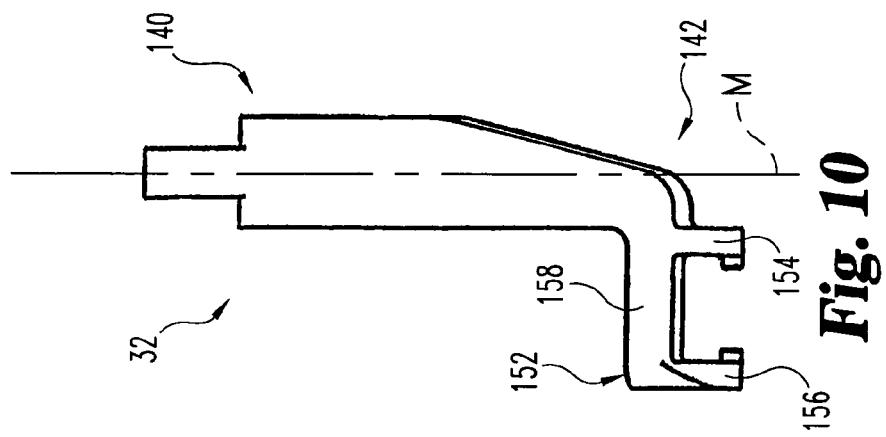
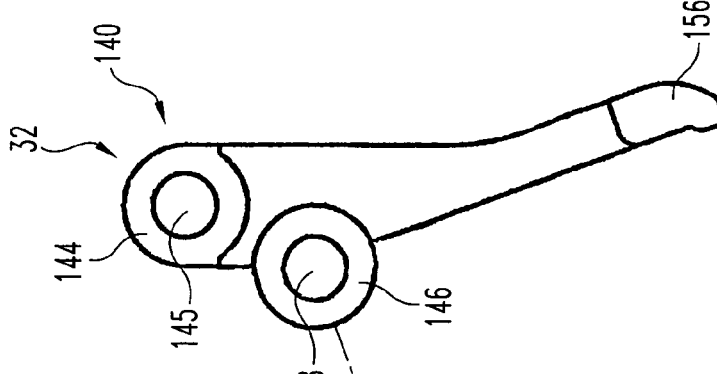
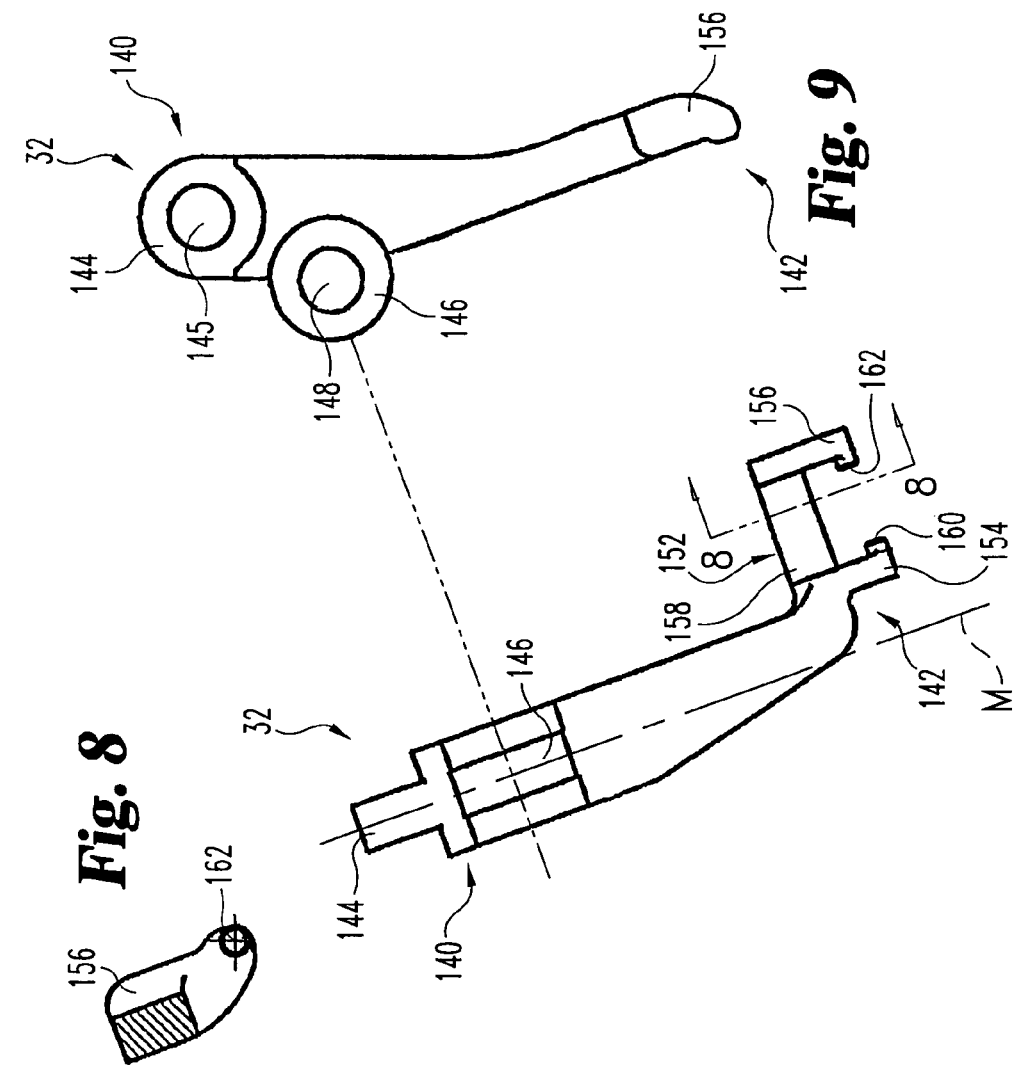

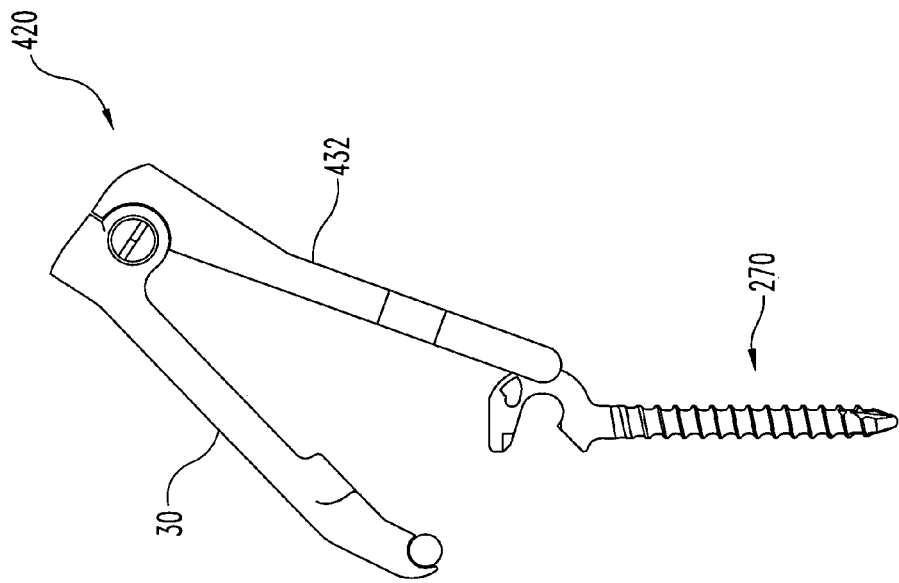
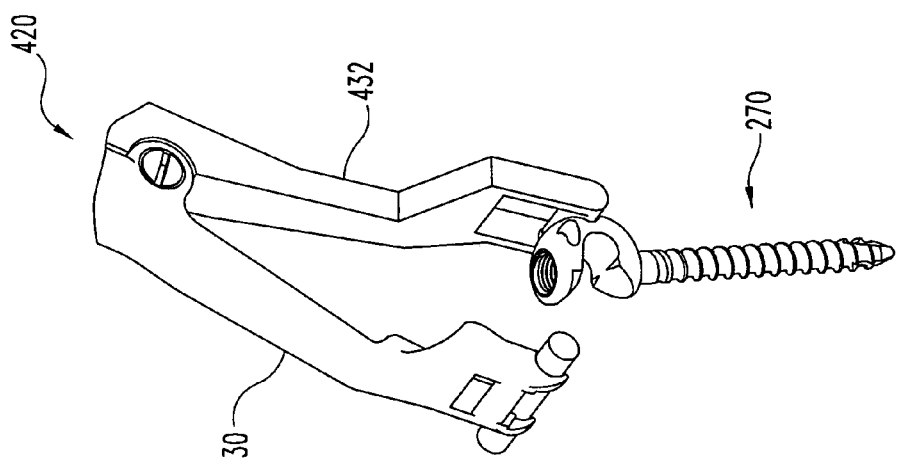

the art to which the invention relates.

REDUCING INSTRUMENT FOR SPINAL SURGERY

CROSS REFERENCE TO RELATED APPLICATIONS

This application is a continuation in part of and claims priority to U.S. patent application Ser. No. 11/043,318, filed Jan. 26, 2005.

BACKGROUND

In orthopedic surgical procedures, it is known to implant devices to support bones or other tissue, to correct deformities, to hold tissues in position for healing after injuries or other surgery, and for other purposes relating to orthopedic health. For example, where correction of a scoliotic or other abnormal curvature or misalignment of the spine is desired, a sturdy rod, plate, or other elongated connecting member can be placed along one or more vertebral segments to support or hold the segments in a corrected position. Bone screws, bone hooks or other fixation implants are attached to vertebrae and connected to the connecting member to secure the connecting member along the spinal column.

Commonly, the fixation implants and the connecting member(s) are placed separately, that is, they are not connected together prior to implantation in the body. For example, bone screws may be implanted into vertebrae first, connectors may be placed on or around the screws (if necessary), and then the connecting member may be placed into the body. The connecting member may be contoured prior to insertion to approximate the curvature desired, or it may be contoured after placement adjacent the spine. In cases where a connecting member and bone screws or other fixation elements are separately placed, the connecting member and screws may be required to be forced toward each other for connection. The process of moving the connecting member and fixation elements toward each other for connection is generally termed "reduction."

Reduction can be accomplished by hand, although the environment and close quarters of a surgical site can make reduction by hand quite difficult. While instruments have been developed to provide a mechanical advantage in reducing or positioning the connecting member relative to an anchor, there remains a need for reducing instruments which are maneuverable relative to the anchor and connecting member to facilitate insertion and manipulation of the connecting member and anchor through the incision or portal in which the reducing instrument is positioned.

BRIEF DESCRIPTION OF THE DRAWINGS

FIG. 3 is another view of the embodiment shown in FIG. 1 in substantially a reverse perspective from that shown in FIG. 1, with certain parts shown in exploded fashion.

FIG. 4 is a top plan view of an embodiment of an arm portion of the embodiment shown in FIG. 1.

FIG. 5 is a side plan view of the embodiment shown in FIG. 4.

FIG. 6 is a partial cross-sectional view of the embodiment shown in FIG. 4, taken along the line 6-6 in FIG. 5 and viewed in the direction of the arrows.

FIG. 7 is a top plan view of an embodiment of an arm portion of the embodiment shown in FIG. 1.

FIG. 8 is a cross-section view of the embodiment shown in FIG. 7, taken along the line 8-8 in FIG. 7 and viewed in the direction of the arrows.

FIG. 9 is a side plan view of the embodiment shown in FIG. 7.

FIG. 10 is a bottom plan view of the embodiment shown in FIG. 7.

FIG. 16A is a perspective view of arm portions of another embodiment of an instrument according to the present invention in relation to an orthopedic rod and an orthopedic implant.

FIG. 16B is a side view of the embodiment shown in FIG. 16A in relation to an orthopedic rod and an orthopedic implant.

DESCRIPTION OF THE ILLUSTRATED EMBODIMENT

Figure 1:
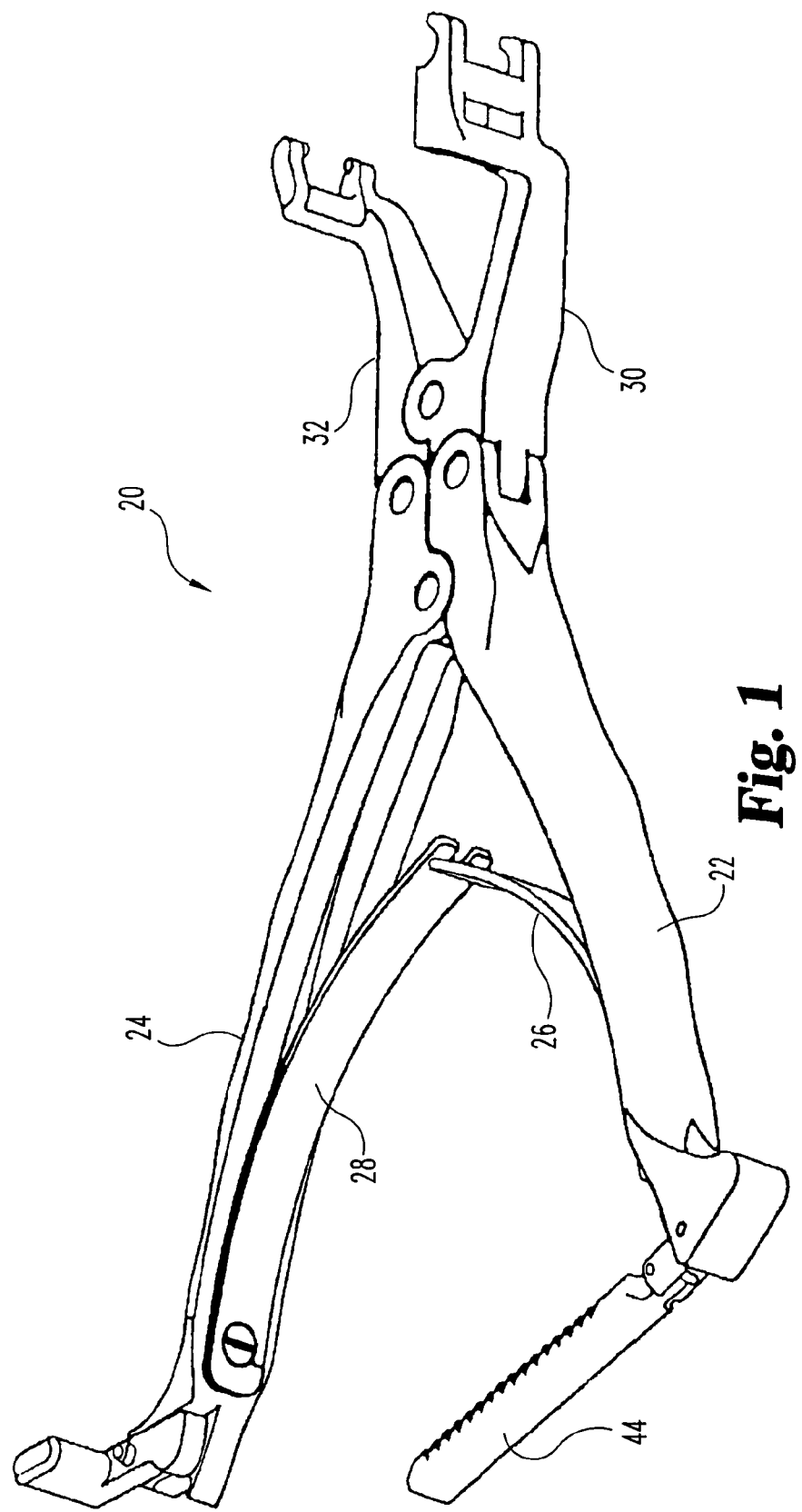
FIG. 1 is a perspective view of an embodiment of an instrument according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein, are contemplated as would normally occur to one skilled in the art to which the invention relates.

Referring generally to the figures, there is shown a reducing instrument 20 that is removably engageable to an implant (e.g. a bone screw or other anchor) and operable to move a rod or other elongated connecting member and the implant toward each other. Reducing instrument 20 includes handle portions 22 and 24, springs 26 and 28, and arm portions 30 and 32. Use of instrument 20 allows good visibility of the implant and remote or sideward positioning of the reducing instrument in alignment with the implant.

Handle portion 22 is generally elongated, having a generally proximal end 40 and a generally distal end 42. Proximal end 40 may be pivotally connected to a toothed bar 44. Toothed bar 44 may be pivotally connected at 46 to a ratchet post 48, having a slot 49, which is pivotally connected to proximal end 40 of handle portion 22. Handle portion 22 may also have a thickened portion 50 to provide a guide for the surgeon's hand, to provide a more stable or secure connection to bar 44 and/or ratchet post 48 if they are present, or for other purposes. Handle portion 22 also includes hole 52 through which handle portion 22 can be connected to handle portion 24. Hole 52 is formed through a part-circular portion 53 that extends from an inside surface of handle portion 22. Portion 53 is thinner than handle portion 22 and is substantially centered on handle portion 22. Hole 52 is generally between proximal end 40 and distal end 42; in the illustrated embodiment hole 52 is relatively close to or adjacent distal end 42. A forked portion 54 is provided at distal end 42, for connecting to an arm portion, as further described below. Forked portion 54 includes holes 55a and 55b, one of which (e.g. 55a) may be threaded.

Handle portion 24 is generally elongated, having a generally proximal end 60 and a generally distal end 62. Proximal end 60 may include a pawl 64 for engaging toothed bar 44. Further, a release lever 66 having a handle 68 and a contact surface 70 may be pivotally connected to proximal end 60. Pressing on handle 68 causes lever 66 to pivot so that contact surface 70 pushes against bar 44 to disengage bar 44 from pawl 64, allowing handle portions 22 and 24 to be spaced apart. Handle portion 24 also includes a groove 72 that makes distal end 62 generally divided or forked. Holes 74a and 74b through which handle portion 24 can be connected to handle portion 22 are provided generally between proximal end 60 and distal end 62, and in the illustrated embodiment adjacent distal end 62. Holes 74a and 74b are formed through part-circular portions 76a and 76b that extend from an inside surface of handle portion 24. Forked distal end 62 also includes holes 78a and 78b for connecting to an arm portion, as further described below. One or both of holes 78a and 78b (e.g. 78a) may be threaded.

In the illustrated embodiment, two leaf springs 26 and 28 are provided to bias handle portions 22 and 24 apart. Spring 26 is attached at or adjacent to an end 90 to handle portion 22 relatively close to proximal end 40, as by a set screw 91 or other connector. Spring 28 is attached at or adjacent to an end 92 to handle portion 24 relatively close to proximal end 60, as by a set screw 91 or other connector. Springs 26 and 28 may interengage, for example via a tongue-and-groove type of engagement. In that configuration, spring 26 may have a tongue portion 94 at the end opposite end 90, and spring 28 may have a groove 96 at the end opposite end 92. When springs 26 and 28 are attached to handle portions 22 and 24, tongue 94 extends into and/or through groove 96. In one particular embodiment, spring 26 may have a tab 98 at or adjacent to end 90 that can be inserted in slot 49 of ratchet post 46. Tab 98 acts as a spring to apply a force on bar 44 to maintain bar 44 in contact with pawl 64. It will be seen that only one leaf spring, such as spring 26 (with or without tongue 94 or tab 98) may be provided for biasing handle portions 22 and 24 apart, or one or more coil or other springs may be provided, or other appropriate structure for biasing handle portions 22 and 24 apart.

Arm portion 30 is an elongated piece having a proximal end 110 and a distal end 112. A relatively thin part-circular portion 114 is provided at or adjacent proximal end 110 with a hole 116 for connecting to hole 54 of handle portion 22. Arm portion 30 also includes a grooved or forked portion 118 generally between proximal end 110 and distal end 112 and in the illustrated embodiment adjacent proximal end 112. Holes 120a and 120b through which arm portion 30 can be connected to arm portion 32 are provided in forked portion 118. Holes 120a and 120b are formed through part-circular portions 121a and 121b that extend from an inside surface of arm portion 30. One or both of holes 120a and 120b (e.g. 120a) may be threaded.

Distal end 112 has a substantially U-shaped portion 122 having extension portions 124 and 126 and cross-pieces 128 and 130. In the illustrated embodiment, extension portions 124 and 126 are substantially parallel to each other, and are substantially perpendicular to cross-pieces 128 and 130. Cross piece 128, in one embodiment, is essentially a lateral extension of the main part of arm portion 30, and may have an indentation 129 through which a screwdriver or other tool can be extended to reach an implant, as for example to apply a locking member such as a set screw to the implant. Cross-piece 130 may include a tab 132 generally extending toward cross-piece 128, which may be at least partially curved, e.g. to provide a surface with a curvature approximating that of an orthopedic rod. Cross-piece 130 may also include an indentation 131 similar to indentation 129 and for a similar purpose. Extension portions 124 and 126 include substantially part-cylindrical hollows 134 and 136, respectively. Hollows 134 and 136 are linear, i.e. the axes of the cylinders of which hollows 134 and 136 are a part are collinear, and hollows 134 and 136 may be of a size and curvature to accommodate an orthopedic rod, e.g. forming a substantially semi-circular (180-degree) section. In a particular embodiment, arm portion 30 has a longitudinal axis L. U-shaped portion 122 is laterally offset from axis L, and may be offset in a direction substantially perpendicular to axis L. U-shaped portion 122 may also be angled with respect to axis L, in a particular embodiment so that U-shaped portion 122 bends toward arm portion 32. Such an angle α may be about 160 degrees in one embodiment.

Arm portion 32 is an elongated piece having a proximal end 140 and a distal end 142. A relatively thin part-circular portion 144 is provided at or adjacent proximal end 140 with a hole 145 for connecting to holes 78a and 78b of handle portion 24. Arm portion 30 also includes another relatively thin part-circular portion 146 with a hole 148 generally between proximal end 140 and distal end 142 and extending from an inside surface of arm portion 32, and in the illustrated embodiment adjacent proximal end 142. Portion 146 fits within forked portion 118 of arm portion 30 so that hole 148 communicates with holes 120a and 120b.

Distal end 142 has a substantially U-shaped portion 152 having extension portions 154 and 156 and cross-piece 158. In the illustrated embodiment, extension portions 154 and 156 are substantially parallel to each other, and are substantially perpendicular to cross-piece 158. Cross piece 158, in one embodiment, is essentially a lateral extension of the main part of arm portion 32. Extension portions 154 and 156 include protrusions 160 and 162 that may be substantially cylindrical. Protrusions 160 and 162 may be substantially linear, i.e. the axes of protrusions 160 and 162 are collinear, and may be relatively thin or short. Protrusions 160 and 162 are for connecting to indentations or hollows in an implant, and therefore they may be configured to accommodate the shape, depth and/or other features of such indentations or hollows.

In a particular embodiment, arm portion 32 has a longitudinal axis M. U-shaped portion 152 can be laterally offset from axis M, and may be offset in a direction substantially perpendicular to axis M. As with portion 122 of arm 30, U-shaped portion 152 could also be angled with respect to axis M in another plane.

As has been suggested above, instrument 20 is assembled generally as follows. Handle portions 22 and 24 are connected by inserting thin portion 53 of handle portion 22 into grooved portion 72 of handle portion 24 so that hole 52 of handle portion 22 communicates with holes 74a and 74b of handle portion 24. An axle, for example a rivet, pin or set screw (e.g. set screws 170 in FIG. 3), can be inserted through holes 52, 74a and 74b and secured so that handle portions 22 and 24 can pivot with respect to each other around such an axle. In an embodiment in which at least one of holes 52, 74a and 74b are at least partially threaded, a set screw may be used as the axle, with the relative advantage that the interacting threads tend to retain the set screw within the holes. In other embodiments, a separate retaining piece, such as a ring to fit into a groove of an axle, or an additional step to retain the axle within the holes, such as swaging or peening part of the axle, can be included.

It will be seen that connection of handle portions 22 and 24 should account for connections of associated parts that may be present. For example, in embodiments in which handle portion 22 includes toothed bar 44 and handle portion 24 includes pawl 64, connection of handle portions 22 and 24 should ensure that bar 44 and pawl 64 connect. In embodiments including lever 66, lever 66 should be proximate to or abut bar 44. As another example, in embodiments in which handle portions 22 and/or 24 include springs, connection of handle portions 22 and 24 should ensure that the one or more springs are proximate to or abut each other or the opposing handle portion so that biasing apart of the handle portions 22 and 24 occurs. In one particular embodiment, as noted above leaf springs 26 and 28 should be arranged so that tongue 94 of spring 26 is at least partially within groove 96 of spring 28.

Arm portions 30 and 32 are connected to each other, and each is connected to one of the handle portions 22 and 24, substantially as described above. Thin portion 146 of arm portion 32 is inserted into grooved portion 118 of arm portion 30 so that hole 148 of arm portion 32 communicates with holes 120a and 120b of arm portion 30. An axle as described above can be inserted through holes 148, 120a and 120b and secured so that arm portions 22 and 24 can pivot with respect to each other around such an axle. A set screw (e.g. set screws 170 in FIG. 3) may be used as such an axle, particularly in embodiments in which at least one of holes 148, 120a and 120b are at least partially threaded. Arm portion 30 is connected to handle portion 22 by inserting thin portion 114 of arm portion 30 into the forked end 54 of handle portion 22, so that hole 116 of arm portion 30 communicates with holes 55a and 55b of handle portion 22. An axle as described above can be inserted through holes 116, 55a and 55b and secured so that arm portion 30 and handle portion 22 can pivot with respect to each other around such an axle. A set screw (e.g. set screws 170 in FIG. 3) may be used as such an axle, particularly in embodiments in which at least one of holes 116, 55a and 55b are at least partially threaded. Arm portion 32 is connected to handle portion 24 by inserting thin portion 144 of arm portion 32 into the forked end of handle portion 24, so that hole 145 of arm portion 32 communicates with holes 78a and 78b of handle portion 24. An axle as described above can be inserted through holes 145, 78a and 78b and secured so that arm portion 32 and handle portion 24 can pivot with respect to each other around such an axle. A set screw (e.g. set screws 170 in FIG. 3) may be used as such an axle, particularly in embodiments in which at least one of holes 145, 78a and 78b are at least partially threaded.

Figure 2:
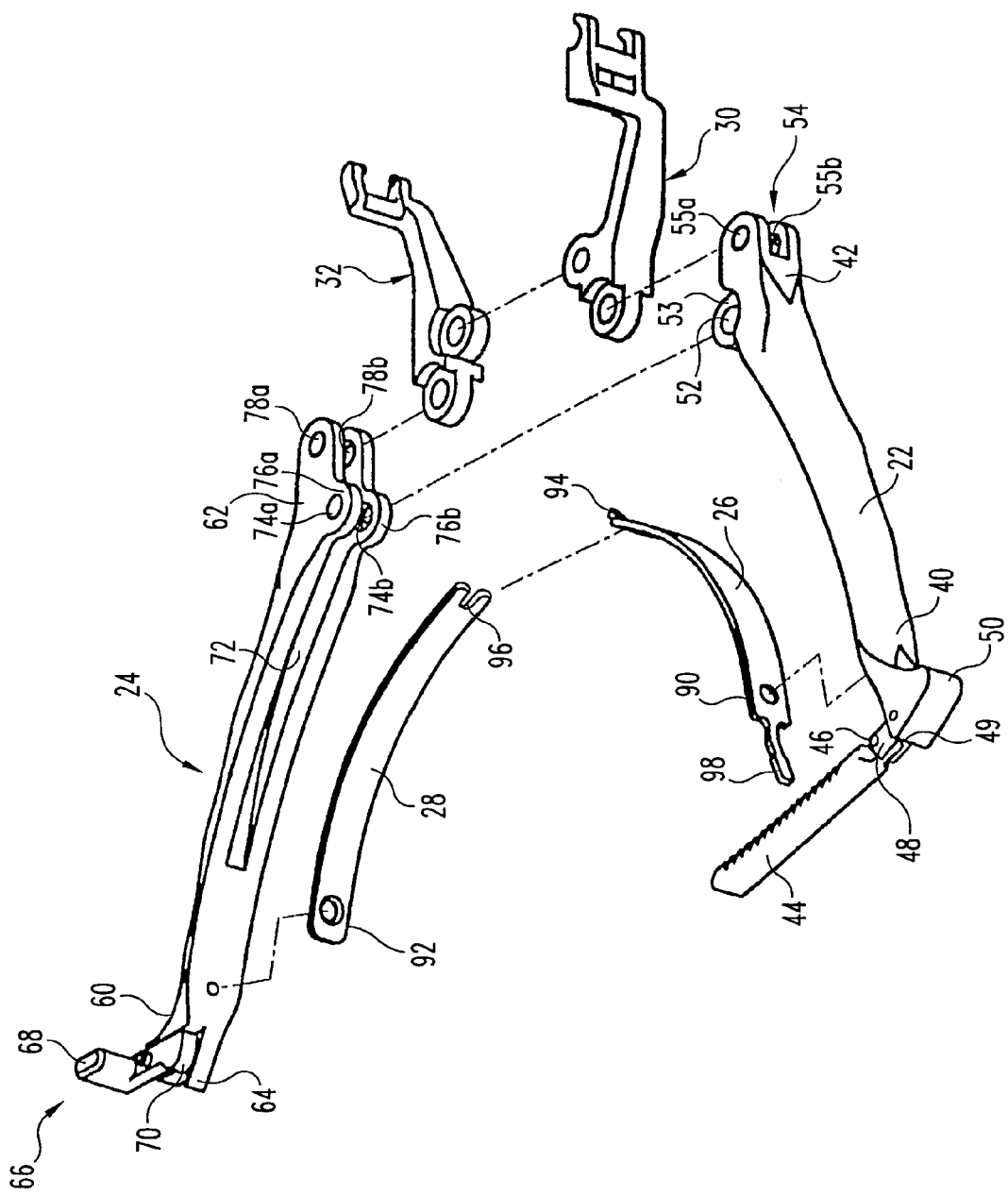
FIG. 2 is an exploded perspective view of the embodiment shown in FIG. 1.

It will be seen that the several portions of embodiments of instrument 20 can be connected in a variety of orders. For example, arm portions 30 and 32 can be connected to each other, then to individual handle portions 22 and 24, with the final connection being that between handle portions 22 and 24. As another example, handle portions 22 and 24 can be connected together first, then to arm portions 30 and 32, with arm portions 30 and 32 being either separate or already connected. The instrument 20 can be assembled as indicated above and in FIGS. 1-3, with distal portions 112 and 142 of arms 30 and 32 offset to the left when handle portion 22 is substantially atop handle portion 24. That positioning occurs when handle portion 22 is directly connected to arm 30 and handle portion 24 is directly connected to arm 32. Instrument 20 can also be assembled so that arm 30 is directly connected to handle portion 24, and arm 32 is directly connected to handle portion 22. In that case, distal portions 112 and 142 of arms 30 and 32 are offset to the left when handle portion 24 is substantially atop handle portion 22, as in FIGS. 11-12.

In using the illustrated embodiment of instrument 20, it will be seen that squeezing handle portions 22 and 24 together causes rotation of handle portions 22 and 24 with respect to each other, so that their respective distal ends 42 and 62 move apart. As distal ends 42 and 62 move apart, the proximal parts of arm portions 30 and 32 also move apart. By virtue of the pivoting connection of arm portions 30 and 32, when the proximal parts of arm portions 30 and 32 move apart, their respective distal portions 112 and 142 move together. Thus, by squeezing handle portions 22 and 24 together, the distal portions 112 and 142 are forced together.

The operation of instrument 20 to engage an implant and rod or other connecting member and seat the connecting member in the implant anchor will now be described with respect to operation on a spinal column. Alternative uses with respect to other bony structures or other tissues can be made. As with other types of orthopedic surgery, an incision is made and access is gained to the surgical site. The approach to the surgical site can be an open approach, i.e. a relatively long incision with retraction of underlying tissue. The instrument disclosed herein can be used in such an approach, or with other surgical techniques.

After access to the surgical site has been obtained, anchors such as those including a receiver member 180 are inserted into bone tissue. Such anchors may be pre-fitted with receiver member 180 or other receiver member embodiment, and such anchors typically include a bone engaging portion 182 and a channel 183 for accommodating part of rod R. Such a channel 183 may point substantially to the side as shown in the figures, or may open to the back of the anchor, or be otherwise oriented. Such receiver members may also be placed on or over engaging portions after engagement of the engaging portions into bone, and may be multi-axial, pivotable or otherwise adjustable with respect to such engaging portions. A connecting member, such as rod R, is inserted into the surgical site, and placed adjacent one or more of the anchors. If not already present, receiver members 180 may be loosely placed on the connecting member prior to insertion of the connecting member to the surgical site. The anchors and connecting member are manipulated so that a part of the connecting member is in or near the each of the anchors. Receiver member 180 can include a pair of branches 184 which generally form channel 183 therebetween. Instrument 20 may be used with a variety of anchors or implants, including those known previously in the art and those disclosed in U.S. patent application Ser. No. 11/000,585 filed on Nov. 30, 2004 and Ser. No. 11/000,846 filed Dec. 1, 2004 and, respectively entitled SIDE-LOADING ADJUSTABLE BONE ANCHOR and SIDE-LOADING BONE ANCHOR, which are incorporated herein by reference in their entireties.

After engagement of the implant to a vertebra, rod R is positioned adjacent the implant. It is contemplated that a number of implants can be positioned and engaged along the spinal column, and the rod engaged in a channel or other area of one of the implants. Due to misalignment of vertebrae, misalignment of the implants, or other conditions, the rod may not be easily or readily positioned in one or more implants.

Figure 11:
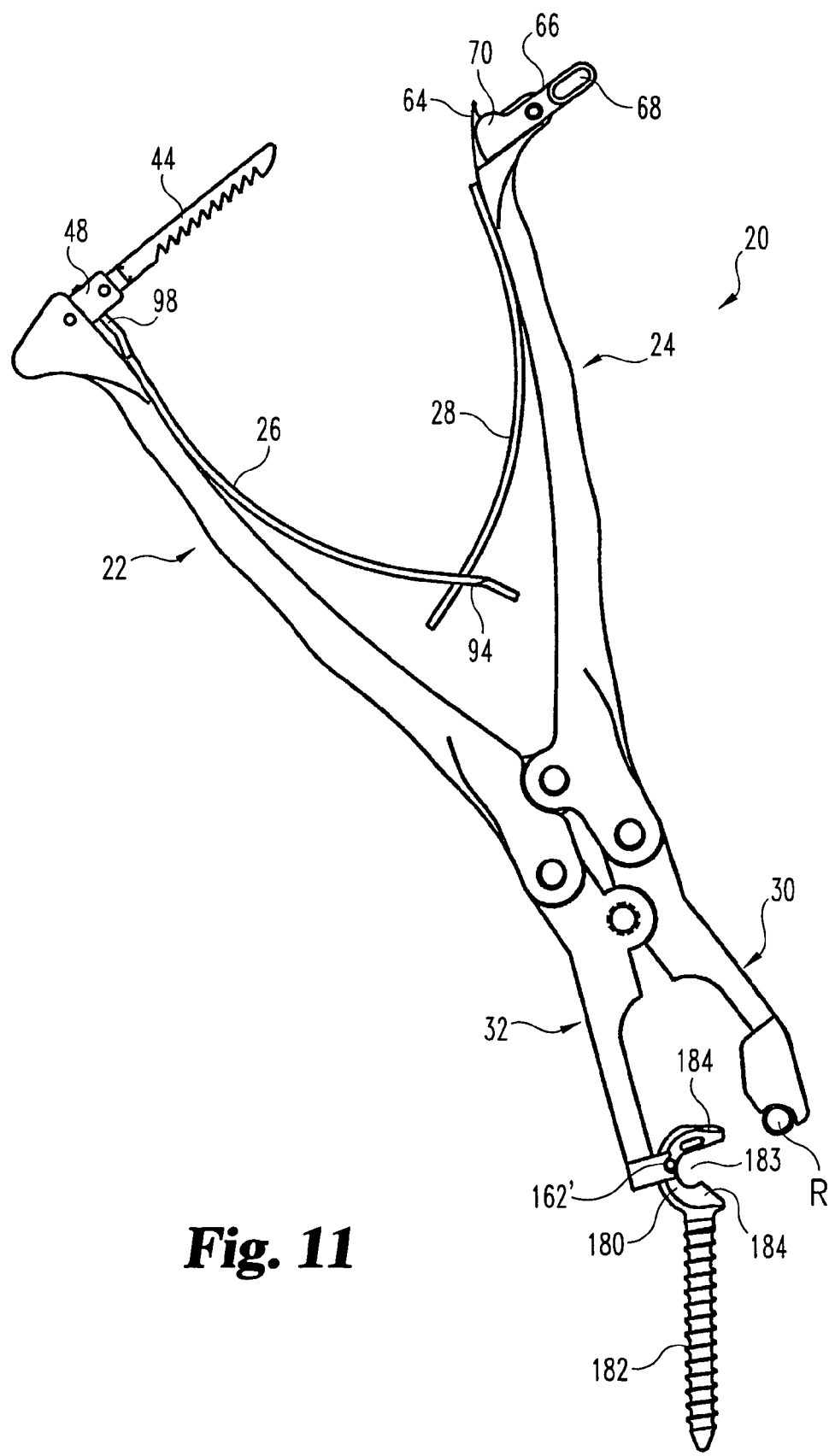
FIG. 11 is a side view of an embodiment of an instrument in relation to an orthopedic rod and an orthopedic implant.
Figure 12:
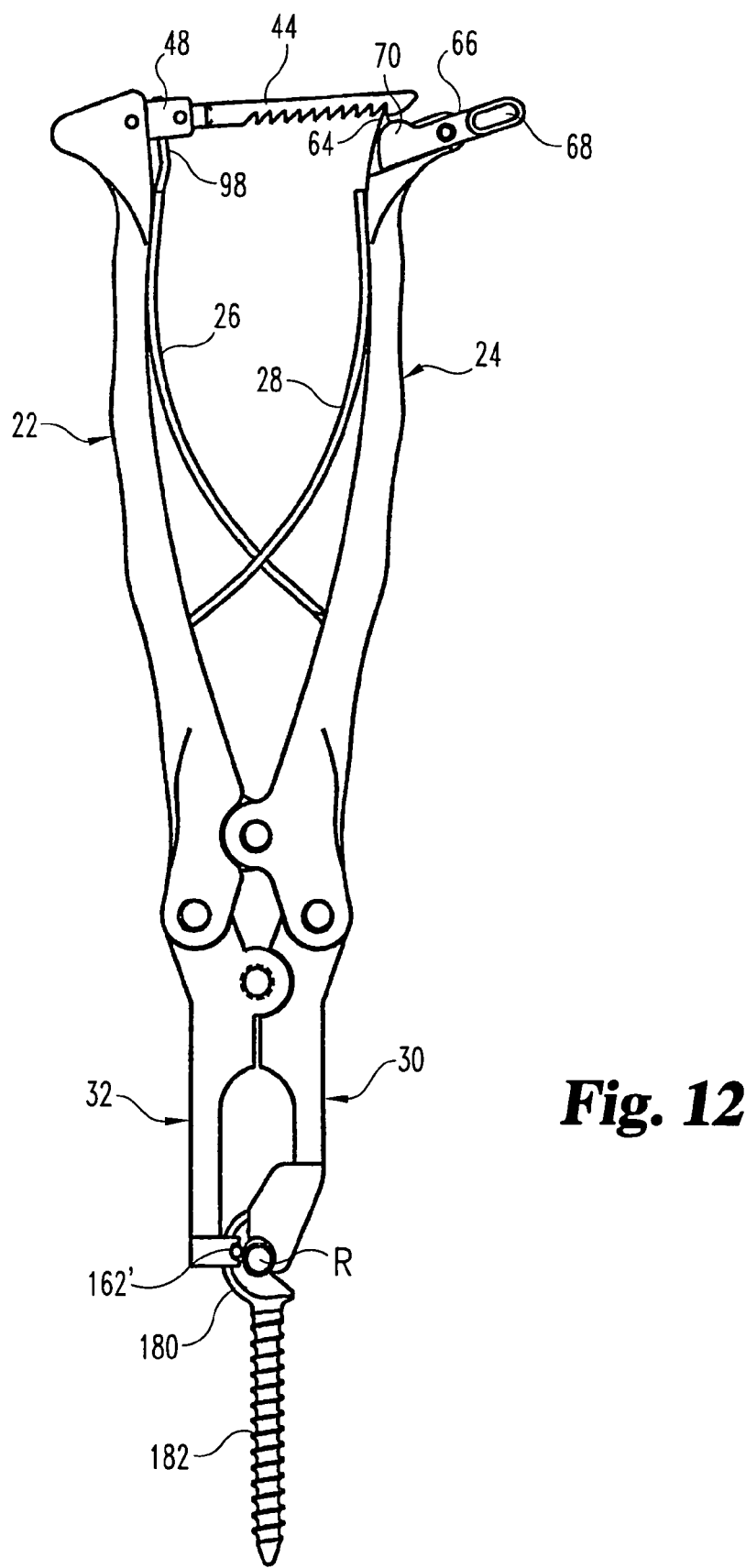
FIG. 12 is a side view of the embodiment shown in FIG. 11 in relation to a reduced orthopedic rod.

Once the rod is adjacent an implant into which the rod is to be placed or seated, instrument 20 may be introduced to reduce or force the rod into the implant. With handle portions 22 and 24 in an unstressed state, i.e. biased away from each other or otherwise spread apart, distal ends 112 and 142 of arm portions 30 and 32 are also spread apart. Distal ends 112 and 142 are placed around the combination of rod R and receiver member 180, so that distal end 112 is adjacent to or abutting a surface of rod R relatively distant from receiver member 180, and distal end 142 is adjacent to or abutting a surface of receiver member 180 relatively distant from rod R. In the embodiment in which distal end 142 includes protrusion(s) 162, such protrusion(s) 162 are inserted or maneuvered into hollow(s) or aperture(s) in receiver member 180. In an alternative embodiment in which receiver member 180 includes one or more side protrusions rather than hollow(s), distal end 142 may be provided with one or more hollows 162', e.g. in extensions 154 and/or 156, to accommodate such protrusions.

Where protrusion(s) 162 or hollow(s) 162' are provided and are substantially rounded or cylindrical and fit with corresponding parts of receiver member 180, as previously described, instrument 20 can pivot or rotate with respect to receiver member 180, as seen in one example in FIGS. 11-12. In that example, a distal portion of arm 32 changes angle with respect to the anchor or implant, as in FIG. 11 that portion of arm 32 is at an oblique angle with respect to engaging portion 182, and in FIG. 12 that portion of arm 32 is substantially parallel to engaging portion 182. The axis of rotation in that example substantially corresponds with protrusion(s) 162 or hollow(s) 162', is different from the axes around which arms 22, 24, 30 and 32 pivot, and is substantially parallel to the axis of channel 183 of receiver member 180. Such pivoting or rotation around protrusion(s) 162 or hollow(s) 162' may force rod R generally toward the bone or substantially perpendicular to a bone surface (downward as seen in FIG. 11) and/or generally toward receiver member 180. In other words, such pivoting may force rod R generally obliquely with respect to a longitudinal axis of implant 180, or in a direction that has at least a component parallel to a longitudinal axis of implant 180. Such pivoting or rotation can occur in this embodiment as may be necessary for rod reduction.

Handle portions 22 and 24 are then squeezed together, which as discussed above forces distal ends 112 and 142 of arm portions 30 and 32 toward each other. Forcing together distal ends 112 and 142 causes rod R and receiver member 180 to move relative to each other so that they become nearer to each other. In many cases, the rod will undergo all or substantially all of such relative movement, and the implant (which is anchored to a bone) will remain relatively stationary. However, it will be appreciated that in some uses the surgeon would prefer the bone and implant to undergo movement toward the rod, for example in some cases of significant vertebral misalignment, and thus instrument 20 can cause such movement of the implant, perhaps with direct manipulation of the bone by the surgeon.

Squeezing of handle portions 22 and 24 is continued until distal ends 112 and 142 of arm portions 30 and 32 force rod R and receiver member 180 together to the extent desired by the surgeon. Toothed bar 44 and pawl 64 interact to maintain handle portions 22 and 24 (and thus arm portions 30 and 32) in a squeezed state, and keeping them from being biased apart if the surgeon's grip should loosen. In this way, instrument 20 can maintain pressure on a rod and implant while the surgeon rests his or her hand or performs another task. As rod R enters receiver member 180, distal end 112 of arm portion 30 approaches the implant (e.g. generally parallel to a bone or bone surface to which the implant is connected), and specifically branches 184 on either side of channel 183 or other area that accommodates the rod. Distal end 112 of arm portion 30 is configured to be able to force rod R into receiver member 180 to the greatest degree desired, because cross pieces 128 and 130 are spaced apart so as to interfere minimally or not at all with branches 184 of receiver member 180. Thus, as distal end 112 approaches branches 184 of receiver member 180, branches 184 enter the gaps between cross pieces 128 and 130, allowing distal end 112 to press the rod toward or to the back of the implant, if that is desired. Through such squeezing of instrument 20 or pivoting of instrument 20 with respect to receiver member 180, or a combination of the two motions, rod R is reduced into channel 183 of receiver member 180.

Once the rod is positioned as the surgeon desires in the implant, the rod is locked into the implant using structure (e.g. set screw, cap, clamp) provided with the implant, as for example by inserting the structure and an appropriate tool through indentations 129 and 131 to the implant. Instrument 20 may be removed from contact with the rod and the implant after such locking, or before if the rod will remain at least approximately in the position desired by the surgeon. When it is desired to remove or loosen the contact of instrument 20 with the rod and/or the implant, the surgeon may press lever 68, which pivots to push toothed bar 44 away from pawl 64. Springs 26 and 28 then act to push handle portions 22 and 24 apart, per their normal bias, and distal portions 112 and 142 of arm portions 30 and 32 come away from the rod and the implant. The surgeon may then move to reduction of the rod into another implant, or may remove instrument 20 from the surgical site to perform other tasks or conclude the surgical procedure.

Figure 13B:
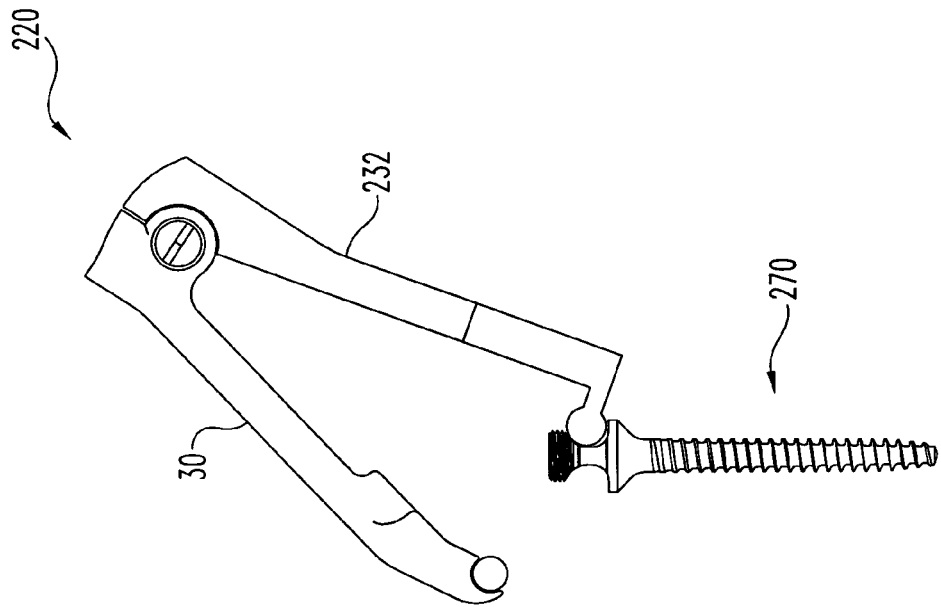
FIG. 13B is a side view of the embodiment shown in FIG. 13A in relation to an orthopedic rod and an orthopedic implant.
Figure 13A:
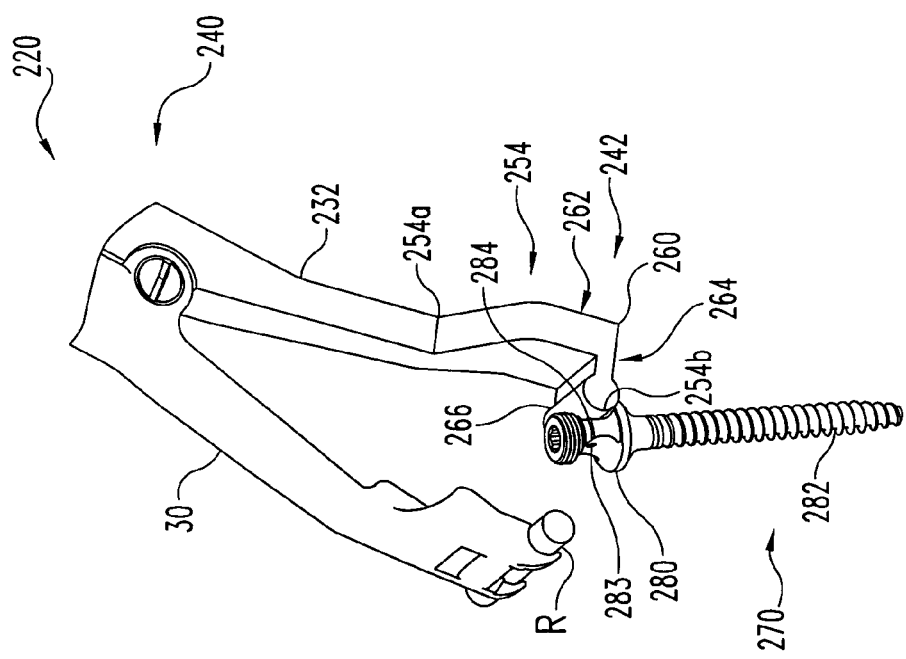
FIG. 13A is a perspective view of arm portions of another embodiment of an instrument according to the present invention in relation to an orthopedic rod and an orthopedic implant.

FIGS. 13A-13B illustrate a portion of a reducing instrument 220 according to another embodiment. In that embodiment, instrument 220 includes arm portions 30 and 232. Instrument 220 may further include handle portions and springs (not shown for clarity), similar in structure and function to handle portions 22 and 24 and springs 26 and 28, and connected as described in with respect to previous embodiments, as are other embodiments described below. Additionally, instrument 220 may include a toothed bar and pawl assembly, as previously described. Arm portion 232 is an elongated piece having a proximal end 240 and a distal end 242. It should be appreciated that arm portion 232 connects with a corresponding handle portion in a substantially similar manner as arm portion 32 connects with handle portion 24.

Distal end 242 has an extension portion 254. Extension portion 254 may generally increase in width from a proximal point 254a to a distal point 254b. In the illustrated embodiment, extension portion 254 includes one section of increasing width; however, it should be appreciated that extension portion 254 can be configured differently. Extension portion 254 includes an approximately 90 degree bend in the illustrated embodiment at bend point 260 between a proximal portion 262 and a distal portion 264. The extension portion 254 may bend in a direction toward an anchor, with distal portion 264 being substantially perpendicular to proximal portion 262. Distal portion 264 includes a section 266, which is generally cylindrical in one particular embodiment, at distal point 254b. Section 266 can be configured to contact an anchor, such as anchor 270. It should be appreciated that instrument 220 may be used with a variety of anchors or implants. Additionally, section 266 can be larger or smaller to fittingly contact various sized channels in various anchors or implants.

In the illustrated embodiment, anchor 270 includes a receiver portion 280 and an engaging portion 282. In certain embodiments, receiver portion 280 includes a first channel 283 and a second channel 284. Part of a rod R can be accommodated in one of channels 283 or 284, depending on which channel is closer to or more exposed to rod R. In the illustrated embodiment, rod R is to be loaded into channel 283, and therefore section 266 of instrument 220 can be inserted into channel 284 in order to reduce or force rod R toward or into channel 283. Receiver portion 280 in the illustrated embodiment is integral with respect to engaging portion 282. A threaded cap (not shown) can thread onto receiver portion 280 to hold rod(s) or other elongated members with respect to receiver member 280.

Figure 14B:
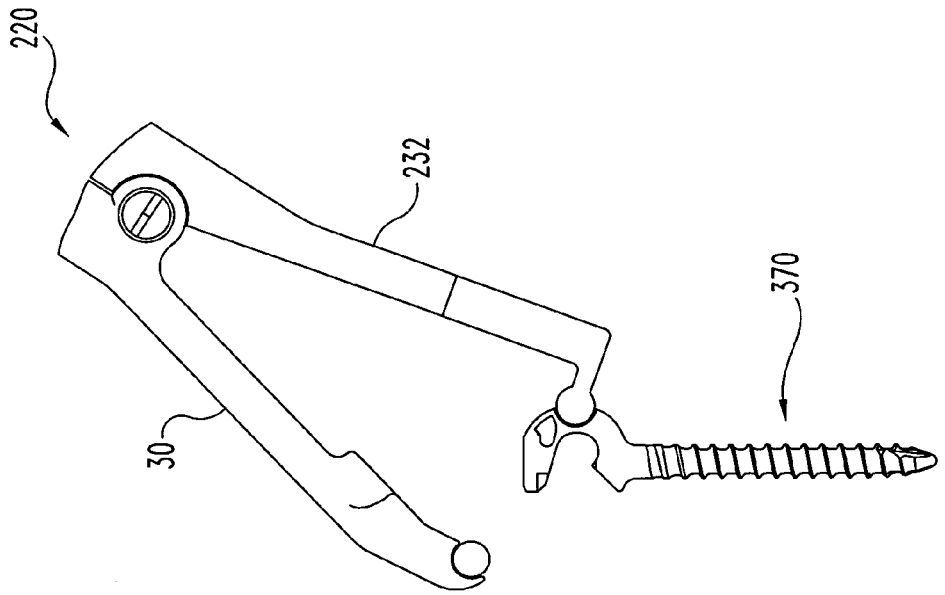
FIG. 14B is a side view of the embodiment shown in FIG. 14A in relation to an orthopedic rod and an orthopedic implant.
Figure 14A:
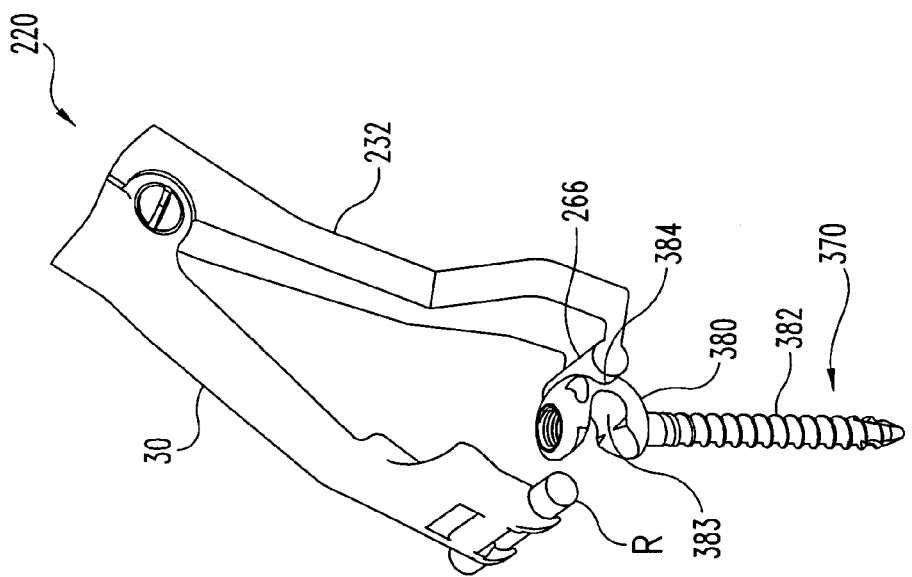
FIG. 14A is a perspective view of arm portions of another embodiment of an instrument according to the present invention in relation to an orthopedic rod and an orthopedic implant.

FIGS. 14A-14B illustrate a portion of instrument 220 used in conjunction with an anchor 370 including a receiver member 380 and an engaging portion 382. Anchor 370 is substantially similar in structure and function to the anchors previously described herein (e.g. those shown in FIGS. 11-12). Receiver member 380 includes a first channel 383 for accommodating part of rod R. Such a channel 383 may point substantially to the side as shown in the figures, or may open to the back of a similar anchor, or be otherwise oriented. In certain embodiments, receiver member 380 also includes a second channel 384 for accommodating part of segment 266.

Figure 15B:
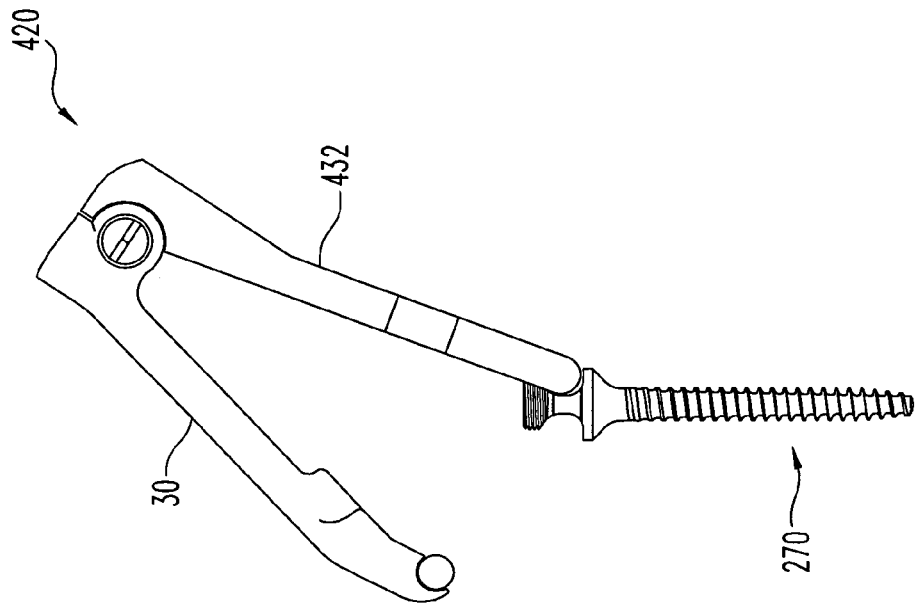
FIG. 15B is a side view of the embodiment shown in FIG. 15A in relation to an orthopedic rod and an orthopedic implant.
Figure 15A:
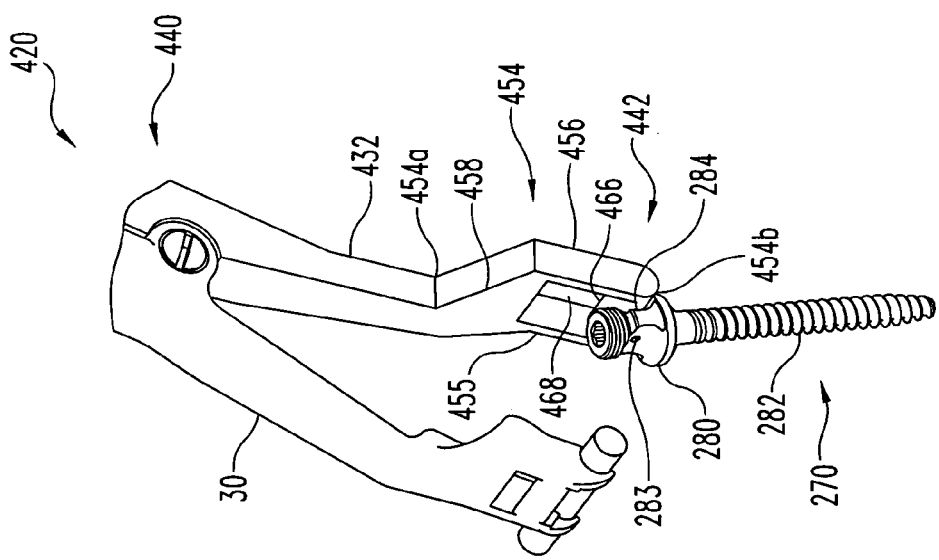
FIG. 15A is a perspective view of arm portions of another embodiment of an instrument according to the present invention in relation to an orthopedic rod and an orthopedic implant.

FIG. 15A-15B illustrate a portion of another embodiment of a reducing instrument 420. Instrument 420 includes arm portions 30 and 432. Instrument 420 may further include handle portions and springs (not shown for clarity), similar in structure and function to handle portions 22 and 24 and springs 26 and 28. Additionally, instrument 420 may include a toothed bar and pawl assembly, as previously described. Arm portion 432 is an elongated piece having a proximal portion 440 and a distal end 442 in the illustrated embodiment. It should be appreciated that arm portion 432 connects with a corresponding handle portion in a substantially similar manner as arm portion 32 connects with handle portion 24.

Distal end 442 includes an extension portion 454. Extension portion 454 may generally increase in width from a proximal point 454a to a distal point 454b. In the illustrated embodiment, extension portion 454 includes one section of increasing width; however, it should be appreciated that extension portion 454 can be configured differently. Extension portion 454 includes extension pieces 455 and 456, and a cross piece 458. In the illustrated embodiment, extension pieces 455 and 456 are substantially parallel to each other and to the body of arm 432, and are substantially perpendicular to cross-piece 458. The extension pieces are connected at distal point 454b with a section 466 that is substantially cylindrical in the illustrated embodiment. Section 466 is configured to contact an anchor, such as anchor 270. Section 466 can be larger or smaller to fittingly contact various sized channels in various anchors or implants.

In the embodiment illustrated in FIGS. 15A and 15B, instrument 420 is used in conjunction with an anchor 270 including receiver member 280 and engaging portion 282. Extension pieces 455. 456, cross-piece 458, and section 466 all generally define a gap 468. Gap 468 is sufficiently sized and configured to admit one of the anchor branches defining second channel 284 of anchor 270.

FIGS. 16A-16B illustrate a portion of instrument 420 used in conjunction with an anchor 370 including receiver member 380 and engaging portion 382. Receiver member 380 also includes second channel 384 for accommodating part of cylindrical segment 466.

Figure 17:
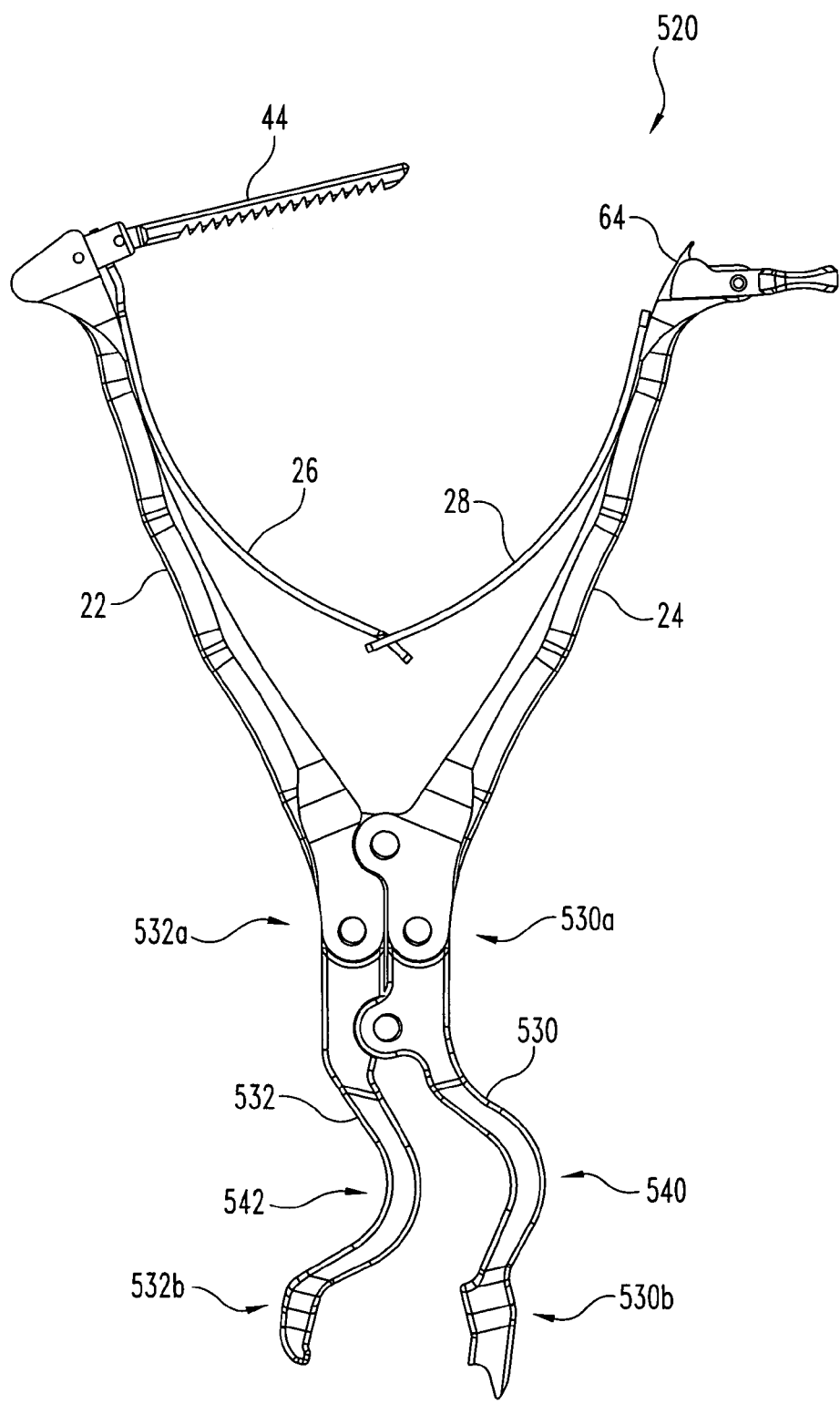
FIG. 17 is a side view of another embodiment of an instrument according to the present invention.

FIG. 17 illustrates another embodiment of a reducing instrument 520. Instrument 520 includes handle portions 22 and 24, springs 26 and 28, and arm portions 530 and 532. Additionally, instrument 520 may include a toothed bar 44 and a pawl 64, as previously described. It should be appreciated that arm portions 530 and 532 connect with handle portions 22 and 24, respectively, in a substantially similar manner as arm portions 30 and 32 connect with the handle portions. Arm portions 530 and 532 have proximal ends 530a and 532a, and distal ends 530b and 532b, respectively. Additionally, arm portions 530 and 532 each include sections of curvature 540 and 542, respectively, positioned between the proximal and distal ends. In certain embodiments, the sections of curvature prevent interference with various tissues and/or other structures or materials within or adjacent to the patient or the surgical site. Distal ends 530b and 532b can be sized and configured in a manner as previously described to contact and engage an anchor and rod or other connecting member and seat the connecting member in the anchor.

In some embodiments, sections 540, 542 are generally positioned in the same plane as the handle portions and arm portions. In other words, sections of curvature 540, 542 generally open in a direction from one arm portion to the other arm portion. In the illustrated embodiment, section 540 opens towards section 542, and concave portions of sections 540 and 542 face in generally the same direction (e.g. the left as shown in FIG. 17). However, it should be appreciated that sections 540, 542 can be arranged, oriented or configured differently.

Figure 18:
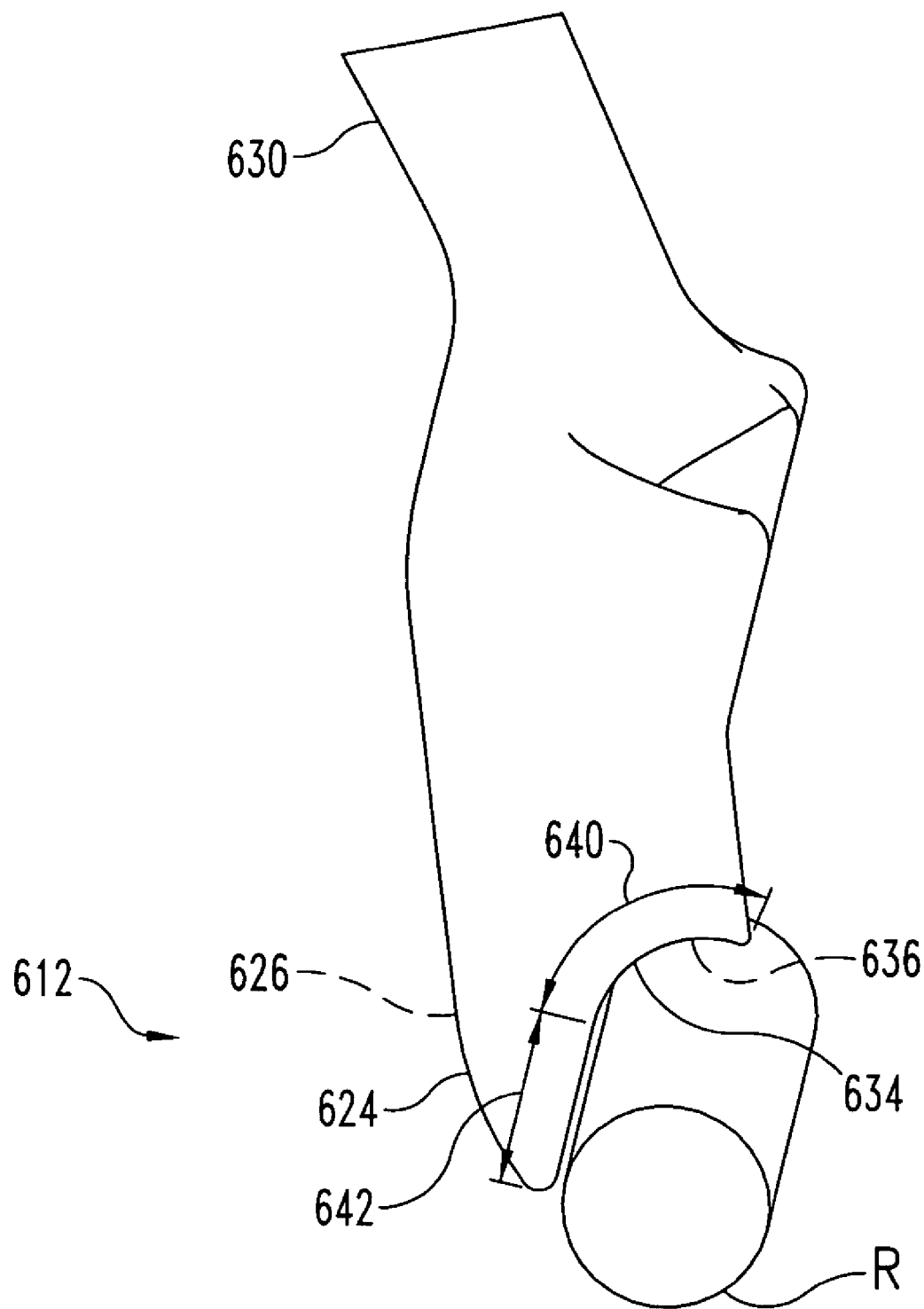
FIG. 18 is a perspective view of an arm portion of another embodiment of an instrument according to the present invention.

FIG. 18 illustrates a portion of an arm 630 of a reducing instrument in another embodiment. Arm 630 includes a proximal end (not shown) that may be similar or identical to ends of arms described above, and a distal end 612. Distal end 612 includes extension portions 624 and 626 (similar to extensions 134 and 136 and those shown in FIGS. 13A, 14A, 15A and 16A), which may include part-cylindrical hollows 634 and 636, respectively. Hollows 634 and 636 are linear, e.g. the axes of the cylinders of which hollows 634, 636 are a part are collinear, and hollows 634, 636 may be of a size and curvature to accommodate an orthopedic rod R. In the illustrated embodiment, hollows 634, 636 each form a substantially quarter-circular (90-degree) section 640, with an adjacent straight segment 642. The absence of a lower lip on one or both hollows 634, 636, as in the illustrated embodiment, can encourage accommodation of an angled rod, e.g. one not perpendicular to extension portions 624 and 626 when their instrument is inserted to the surgical site, or other elongated members of various configurations.

Figure 19:
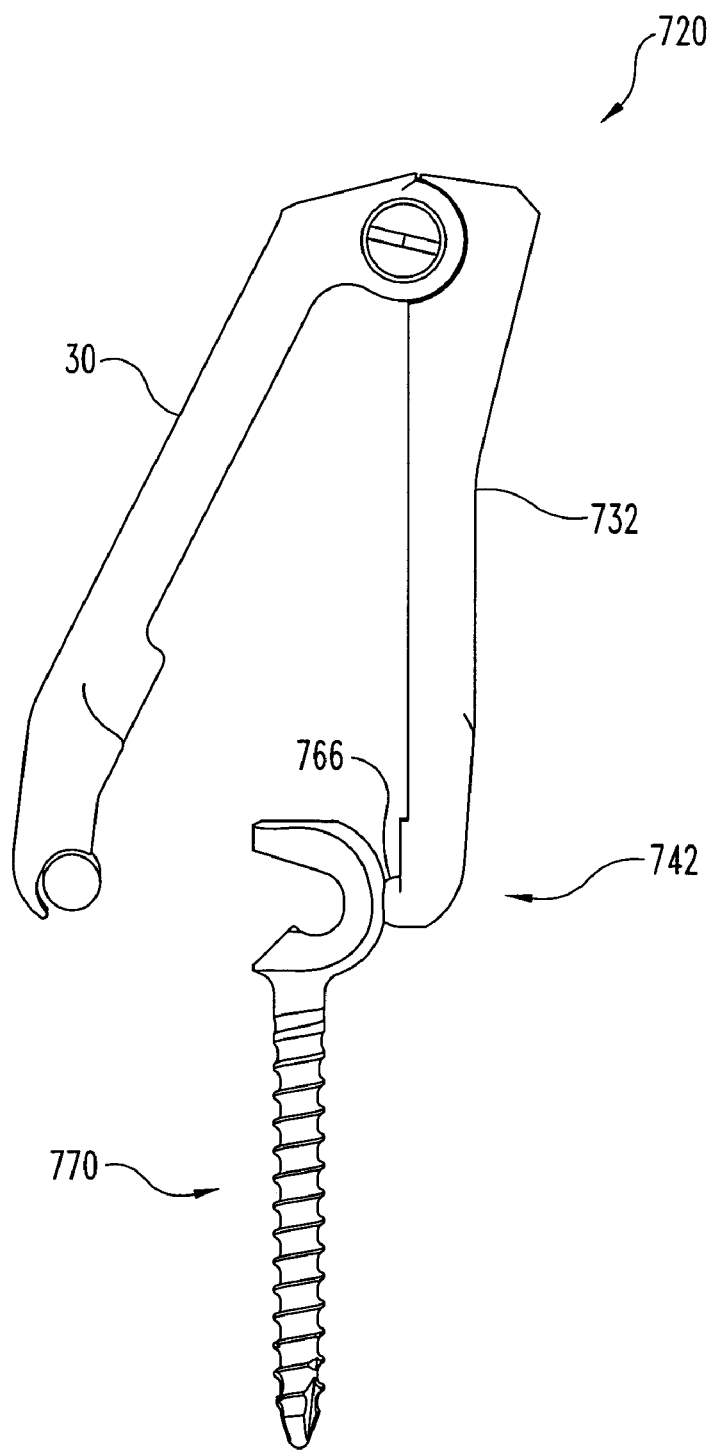
FIG. 19 is side view of arm portions of another embodiment of an instrument according to the present invention in relation to an orthopedic rod and an orthopedic implant.

FIG. 19 illustrates a portion of a reducing instrument 720 in another embodiment. Instrument 720 includes arm portions 30 and 732. Instrument 720 may further include handle portions and springs (not shown for clarity), similar in structure and function to handle portions 22 and 24 and springs 26 and 28. Additionally, instrument 720 may include a toothed bar and pawl assembly, as previously described. Arm portion 732 is an elongated piece having a proximal end 740 and a distal end 742. It should be appreciated that arm portion 732 connects with a corresponding handle portion in a substantially similar manner as arm portion 32 connects with handle portion 24. A protrusion 766 is disposed on arm portion 732 at distal end 742. In the illustrated embodiment, protrusion 766 is spherical; however, it should be appreciated that protrusion 766 can be configured differently. Protrusion 766 is configured to contact an anchor 770, similar in configuration to anchor 370. In certain embodiments, anchor 770 can include a recess configured to receive a portion of protrusion 766. In one embodiment, protrusion 766 extends the width of arm portion 732. In another embodiment, arm portion 732 may include two extension portions, and a protrusion such as protrusion 766, disposed on each distal end of the extension portions.

Figure 20:
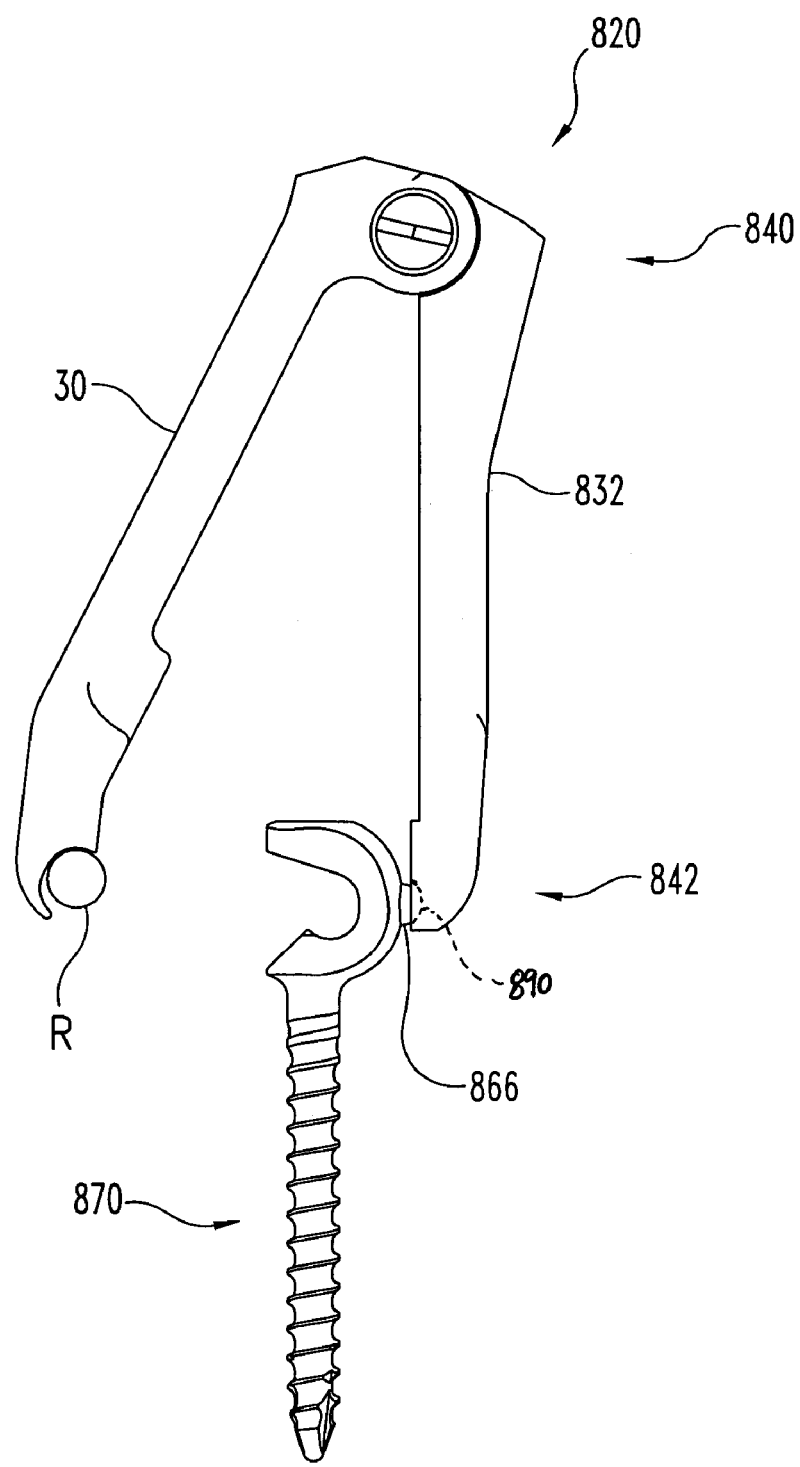
FIG. 20 is side view of arm portions of another embodiment of an instrument according to the present invention in relation to an orthopedic rod and an orthopedic implant.

FIG. 20 illustrates a portion of a reducing instrument 820 according to another embodiment. Instrument 820 includes arm portions 30 and 832. Instrument 820 may further include handle portions and springs (not shown for clarity), similar in structure and function to handle portions 22 and 24 and springs 26 and 28. Additionally, instrument 820 may include a toothed bar and pawl assembly, as previously described. Arm portion 832 is an elongated piece having a proximal end 840 and a distal end 842. It should be appreciated that arm portion 832 connects with a corresponding handle portion in a substantially similar manner as arm portion 32 connects with handle portion 24. In the illustrated embodiment, a protrusion 866 is disposed on an anchor 870, similar in configuration to anchor 370. Protrusion 866 is shown to be spherical in one embodiment; however, it should be appreciated that protrusion 866 can be configured differently. Protrusion 866 is positioned on the receiver portion of anchor 870, opposite a channel for receiving a portion of an orthopedic rod R or other elongated member. In certain embodiments, the arm portion includes a recess 890 at distal end 842 configured to receive a portion of protrusion 866.

In an alternative embodiment, arm portion 832 of reducing instrument 820 could include a recess configured to receive a portion of a receiver member of an anchor (e.g. anchor 370). In such an embodiment, the recess in the arm portion would fittingly contact a portion of a receiver member of an anchor, the portion being opposite a channel configured to receive an orthopedic rod. In such an embodiment, protrusion 866 may be absent and the recess in the arm portion partially surrounds the receiver member of the anchor. The recess may include a generally spherical configuration or another such appropriate configuration. In such an embodiment, the recess in the arm portion, and the portion of the receiver member contacting the recess in the arm portion, would generally include similar degrees of curvature so that the arm portion would fittingly contact the anchor.

The assembly and operation of reducing instruments 220, 420, 520, 720, and 820 is substantially similar to the assembly and operation of reducing instrument 120 described above. As an example, the arm portions of the reducing instruments 220, 420, 520, 720, and 820 connect to each other in a substantially similar manner as arm portions 30 and 32 connect together.

Regarding the operation of embodiments of reducing instruments 220, 420, 520, 720, and 820, after access to the surgical site has been obtained, anchors such as those including receiver members 280 or 380 are inserted into bone tissue. Such receiver members may also be placed on or over engaging portions after engagement of the engaging portions into bone, and may be multi-axial, pivotable or otherwise adjustable with respect to such engaging portions. A connecting member, such as rod R, is inserted into the surgical site, and placed adjacent one or more of the anchors. The anchors and connecting member are manipulated so that a part of the connecting member is in or near the each of the anchors, and such manipulation can be accomplished using embodiments of reducing instruments such as those described above. The instruments may be used with a variety of anchors or implants, including those known previously in the art and those described above.

During operation, the embodiments of reducing instruments described above operate generally similarly to each other, and therefore for simplicity operation of the embodiment of instrument 220 will be described. These descriptions of operation and those given above apply to other embodiments as well. Instrument 220 engages an implant and rod or other connecting member to insert or seat the connecting member in the implant. Such operation can include reducing or forcing the rod into the implant once the rod is positioned adjacent the implant into which the rod is to be placed or seated. The distal ends of the arm portions are placed around the rod and the receiver member of the anchor. The handle portions are squeezed together, forcing the distal ends of the arm portions towards each other, and causing the rod and the receiver member to become nearer to each other and eventually for the rod to be inserted into the receiver member. The toothed bar and pawl assemblies, if present, interact to maintain the handle portions squeezed together. Once the rod is positioned, the rod can be locked into the implant anchor. A lever, if provided, can be pressed to disengage the toothed bar from the pawl, and the handle portions can be moved apart (e.g. by springs, if present) to enable removal of instrument 220 from the surgical site. Thus, through squeezing of an embodiment of the instrument or pivoting of an embodiment of the instrument with respect to an anchor or a receiver member or portion of an anchor, or a combination of the two motions, a rod may be reduced into a channel of the anchor or its receiver member.

As described above, the anchors and connecting member may be positioned in or along one or more parts of the spine, including the cervical, thoracic, lumbar and/or sacral portions. Although the use of embodiments of instruments is described in the above context, such embodiments and others could be used with a variety of screws, hooks or other fixation implants, or in connection with orthopedic implants in parts of the body other than the spine.

The above embodiments and others may be made of stainless steel, certain hard plastics, or other materials that are compatible with surgical procedures and the implants and rods with which they are used. Features particularly described above in connection with one embodiment may be used or incorporated into other embodiments. For example, arm configurations or distal end configurations shown in one figure could be used in connection with apparatus shown in other figures.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A rod reducing apparatus comprising:
   first and second handle elements each having a proximal portion and a distal end, said handle elements being pivotally connected to each other adjacent said distal ends of said handle elements;

at least one spring connected to at least one of said handle elements and between said handle elements, whereby said handle elements are biased apart; and first and second arm elements each having a proximal end and a distal end, said arm elements being pivotally connected to each other between said ends, said proximal end of said first arm element being pivotally connected to said distal end of said first handle element, and said proximal end of said second arm element being pivotally connected to said distal end of said second handle element, whereby bringing together said first and second handle elements brings together said distal ends of said arm elements;

said distal end of said first arm element having at least one extension portion having a proximal end and a distal end, wherein at least one engagement member is positioned at said distal end of said at least one extension portion and configured to contact an orthopedic bone anchor having two spaced apart branches defining a channel therebetween sized to receive a spinal rod;

said distal end of said second arm element having a substantially U-shaped portion, said U-shaped portion having two extension portions substantially parallel to said second arm element and a pair of cross-pieces joining said extension portions with a gap formed between said pair of cross-pieces, said U-shaped portion connecting to the remainder of said second arm element adjacent one or both of one of said cross-pieces and one of said extension portions, said extension portions having respective distal ends, said distal ends of said extension portions of said second arm element each including a substantially part-cylindrical hollow, said hollows being substantially coaxial and having a radius equal to or larger than the radius of a the spinal rod;

wherein said at least one engagement member defined by said at least one extension portion of said first arm element is pivotally engaged with said orthopedic bone anchor at a pivot engagement location defining a pivot axis, and wherein said first arm element pivots with respect to said orthopedic implant at said pivot engagement location about said pivot axis, and said first and second arm elements are operable to force the spinal rod and the orthopedic bone anchor together, and wherein one of the branches of the orthopedic bone anchor is generally aligned with said gap between said cross-pieces of said second arm element when said spinal rod is positioned within said channel.

2. The apparatus of claim 1, wherein one of said cross-pieces is more proximal to said handle portions and one of said cross-pieces is more distal from said handle portions, and said more distal cross-piece includes a tab portion.

3. The apparatus of claim 2, wherein said tab portion is at least partially curved.

4. The apparatus of claim 1, wherein said U-shaped portion of said second arm element is angled toward said first arm element.

5. The apparatus of claim 4, wherein said second arm element has a longitudinal axis, and the angle between said axis and said U-shaped portion of said second arm element is about 160 degrees.

6. The apparatus of claim 1, wherein said distal end of said first arm element has two extension portions positioned substantially parallel to said first arm element and a cross-piece joining said extension portions, wherein said at least one engagement member includes two protrusions, each distal end of said two extension portions including one of said protrusions, said protrusions substantially facing each other.

7. The apparatus of claim 1, wherein said at least one engagement member is a single cylindrical portion positioned at said distal end of said at least one extension portion of said first arm element.

8. The apparatus of claim 1, wherein said at least one engagement member is a piece defining a hollow positioned at said distal end of said at least one extension portion of said first arm element.

9. The apparatus of claim 8, wherein said anchor includes a protrusion, said hollow being configured to receive at least a portion of said protrusion.

10. The apparatus of claim 1, wherein said first and second arm elements each include a curved portion between said distal and proximal ends of said arm elements, wherein said curved portions open in a direction from one arm element towards the other arm element.

11. The apparatus of claim 1, wherein said part-cylindrical hollows each include a circumference of about one-fourth the circumference of a circle.

12. A rod reducing apparatus comprising:

first and second handle elements each having a proximal portion and a distal end, said handle elements being pivotally connected to each other adjacent said distal ends of said handle elements;

at least one spring connected to at least one of said handle elements and between said handle elements, whereby said handle elements are biased apart; and first and second arm elements each having a proximal end and a distal end, said arm elements being pivotally connected to each other between said ends, said proximal end of said first arm element being pivotally connected to said distal end of said first handle element, and said proximal end of said second arm element being pivotally connected to said distal end of said second handle element, whereby bringing together said first and second handle elements brings together said distal ends of said arm elements;

said distal end of said first arm element having at least one extension portion having a proximal end and a distal end, wherein a cylindrical portion is positioned proximal said distal end of said at least one extension portion and configured to contact an anchor, said cylindrical portion being substantially linear and arranged along a pivot axis positioned substantially perpendicular to said at least one extension portion, said cylindrical portion configured to accommodate a corresponding cylindrical-shaped feature of said anchor, said cylindrical portion pivotably engaged with said cylindrical-shaped feature at a pivot engagement location defining said pivot axis, wherein said first arm element pivots with respect to said anchor at said pivot engagement location about said pivot axis;

said distal end of said second arm element having a substantially U-shaped portion, said U-shaped portion having two extension portions substantially parallel to said second arm element and a pair of cross-pieces joining said extension portions, said U-shaped portion connecting to the remainder of said second arm element adjacent one or both of one of said cross-pieces and one of said extension portions, said extension portions having respective distal ends, said distal ends of said extension portions each including a substantially part-cylindrical hollow, said hollows being substantially coaxial and having a radius equal to or larger than the radius of a spinal rod.

13. The apparatus of claim 12, wherein said first and second arm elements each include a curved portion between said distal and proximal ends of said arm elements, wherein said curved portions are positioned in a first plane, both of said handle elements being positioned in a second plane, wherein said first and second planes are parallel.

14. The apparatus of claim 12, wherein said part-cylindrical hollows each include a circumference of about one-fourth the circumference of a circle.

15. The apparatus of claim 14, wherein each of said distal ends of said extension portions of said second arm element includes a straight segment adjacent said part-cylindrical hollow.

16. The apparatus of claim 12, wherein said extension portion of said first arm element includes a bend of about 90 degrees, said cylindrical portion being offset from said extension portion in a direction toward said second arm element.

17. The apparatus of claim 12, wherein said distal end of said first arm element includes two extension portions substantially parallel to said first arm element and a first cross-piece joining said extensions portions at said proximal ends, wherein said cylindrical portion is a second cross-piece joining said distal ends of said extension portions.

18. The apparatus of claim 17, wherein the apparatus is used in conjunction with an orthopedic bone anchor having two spaced branches, and said first cross-piece and said cylindrical portion are separated by a gap sufficient to admit one of said branches.

19. A rod reduction apparatus comprising:
a first arm portion adapted to connect to an orthopedic rod, said arm portion including two extensions and two cross-pieces substantially perpendicular to said extensions, said extensions and said cross-pieces forming a gap, said extensions each having a hollow for accommodating the orthopedic rod; and
a second arm portion adjacent said first arm portion, said second arm portion being adapted to connect to an orthopedic implant having two spaced apart branches defining a channel therebetween sized to receive the orthopedic rod, said second arm portion including one or more extension portions having distal and proximal ends, wherein a cylindrical portion is positioned proximal said distal ends and configured to contact the orthopedic implant, said cylindrical portion pivotally engaged with said orthopedic implant at a pivot engagement location defining a pivot axis, wherein said first arm element pivots with respect to said orthopedic implant at said pivot engagement location about said pivot axis substantially parallel to an axis of said channel;
whereby said arm portions are operable to force the orthopedic rod and the orthopedic implant together.

20. The apparatus of claim 19, wherein one of said cross-pieces of said first arm portion is adjacent said hollows of said extensions and includes a tab portion that is at least partially curved, said curve being configured approximately the same as said hollows.

21. The apparatus of claim 19, wherein said hollows form a substantially quarter-circular section.

22. The apparatus of claim 19, wherein said first arm portion includes two extension portions substantially parallel to said first arm portion, wherein said cylindrical portion is a first cross-piece joining said distal ends of said extension portions.

23. The apparatus of claim 22, wherein a second cross-piece joins said proximal ends of said extension portions, said second cross-piece and said cylindrical portion defining a gap wide enough to allow a branch of the orthopedic implant to at least partially pass through.

24. The apparatus of claim 19, wherein said first arm portion includes one extension portion, said one extension portion including a bend of about 90 degrees so that said cylindrical portion is offset from said extension portion in a direction toward said second arm portion.

25. The apparatus of claim 19, wherein said first and second arm portions each include a curved section between the ends of said arm portions, wherein said curved sections open in a direction from one arm portion to the other arm portion.

26. An apparatus for reducing an elongated member to an orthopedic implant having a channel for receiving the elongated member, comprising:
a first portion adapted to be connected to the implant, said first portion being pivotable with respect to the implant around an axis substantially parallel to an axis of the implant channel when said first portion is connected to the implant;
a second portion adapted to contact the rod, said second portion being connected to said first portion so that said portions can be forced generally toward each other, wherein when said second portion contacts the rod, forcing said portions generally toward each other urges the rod generally toward the implant, and pivoting said first portion around the implant urges said rod toward general alignment with the implant channel;
wherein when said second portion contacts the rod and the implant is connected to a bone, forcing said portions generally together pushes the rod generally parallel to a bone surface, and pivoting said first portion around the implant pushes the rod generally perpendicular to the bone.

27. A rod reduction apparatus comprising:
a first arm portion adapted to connect to an orthopedic rod, said arm portion including two extensions and two cross-pieces substantially perpendicular to said extensions, said extensions and said cross-pieces forming a gap, said extensions each having a hollow for accommodating the orthopedic rod; and
a second arm portion adjacent said first arm portion, said second arm portion being adapted to connect to an orthopedic implant having two spaced apart branches defining a channel therebetween sized to receive the orthopedic rod, said second arm portion including one or more extension portions having distal and proximal ends, wherein a cylindrical portion is positioned proximal said distal ends and configured to contact the orthopedic implant, said cylindrical portion pivotally engaged with said orthopedic implant wherein said first arm element pivots with respect to said orthopedic implant about a pivot axis substantially parallel to an axis of said channel, wherein said cylindrical portion is substantially linear and is positioned substantially perpendicular to said one or more extension portions;
whereby said arm portions are operable to force the orthopedic rod and the orthopedic implant together.

28. A rod reduction apparatus comprising:
a first arm portion adapted to connect to an orthopedic rod, said arm portion including two extensions and two cross-pieces substantially perpendicular to said extensions, said extensions and said cross-pieces forming a gap, said extensions each having a hollow for accommodating the orthopedic rod; and
a second arm portion adjacent said first arm portion, said second arm portion being adapted to connect to an orthopedic implant having two spaced apart branches defining a channel therebetween sized to receive the orthopedic rod, said second arm portion including one or more extension portions having distal and proximal ends, wherein a cylindrical portion is positioned proximal said distal ends and configured to contact the orthopedic implant, said cylindrical portion pivotally engaged with said orthopedic implant wherein said first arm element pivots with respect to said orthopedic implant about a pivot axis substantially parallel to an axis of said channel, wherein said cylindrical portion is configured to accommodate a corresponding cylindrical-shaped feature of said orthopedic implant, said cylindrical portion pivotally engaged with said cylindrical-shaped feature wherein said second arm portion pivots with respect to said orthopedic implant about said pivot axis;

whereby said arm portions are operable to force the orthopedic rod and the orthopedic implant together.

29. An apparatus for reducing an elongated member to an orthopedic implant having a channel for receiving the elongated member, comprising:

a first portion adapted to be connected to the implant, said first portion being pivotable with respect to the implant around an axis substantially parallel to an axis of the implant channel when said first portion is connected to the implant;

a second portion adapted to contact the rod, said second portion being connected to said first portion so that said portions can be forced generally toward each other, wherein when said second portion contacts the rod, forcing said portions generally toward each other urges the rod generally toward the implant, and pivoting said first portion around the implant urges said rod toward general alignment with the implant channel;

wherein said first portion is pivotally engaged with said implant to provide said pivoting of said first portion around said implant and wherein said first portion includes at least one pivot engagement member arranged along a pivot axis substantially parallel to said axis of said implant channel, said at least one pivot engagement member pivotally engaged with a corresponding portion of said implant at a pivot engagement location defining said pivot axis, and wherein said at least one pivot engagement member pivots with respect to said implant at said pivot engagement location about said pivot axis.

30. The apparatus of claim 29, wherein said first portion is a part of a first arm, said second portion is a part of a second arm, said arms being hingedly connected, and further comprising a handle portion including one or more handle elements, said handle portion connected to said arms so that activating said handle portion forces said end portions of said arms generally toward each other.

31. The apparatus of claim 29, wherein when said second portion contacts the rod and the implant is connected to a bone so that the implant extends in a first direction away from the bone, forcing said portions generally toward each other pushes the rod generally obliquely or perpendicularly with respect to said first direction, and pivoting said first portion around the implant pushes the rod in a direction having at least a component that is parallel to said first direction.

* * * * *